United States Patent
Sun et al.

(10) Patent No.: US 10,299,896 B2
(45) Date of Patent: May 28, 2019

(54) THREE-DIMENSIONAL FABRICATING MATERIAL SYSTEMS AND METHODS FOR PRODUCING LAYERED DENTAL PRODUCTS

(71) Applicant: DENTSPLY SIRONA Inc., York, PA (US)

(72) Inventors: Benjamin J Sun, York, PA (US); Dan Ammon, York, PA (US)

(73) Assignee: DENTSPLY SIRONA Inc., York, PA (US)

( * ) Notice: Subject to any disclaimer, the term of this patent is extended or adjusted under 35 U.S.C. 154(b) by 35 days.

(21) Appl. No.: 15/628,194

(22) Filed: Jun. 20, 2017

(65) Prior Publication Data

US 2017/0360534 A1 Dec. 21, 2017

Related U.S. Application Data

(60) Provisional application No. 62/352,320, filed on Jun. 20, 2016.

(51) Int. Cl.
*A61K 6/08* (2006.01)
*A61C 13/00* (2006.01)
(Continued)

(52) U.S. Cl.
CPC ...... *A61C 13/0019* (2013.01); *A61C 13/0004* (2013.01); *A61C 13/0013* (2013.01);
(Continued)

(58) Field of Classification Search
None
See application file for complete search history.

(56) References Cited

U.S. PATENT DOCUMENTS

| 4,533,446 A * | 8/1985 | Conway ............... C08F 290/06 |
| | | 156/273.3 |
| 5,059,266 A | 10/1991 | Yamane |
| | (Continued) | |

FOREIGN PATENT DOCUMENTS

| WO | 2014078537 A1 | 5/2014 |
| WO | WO-2014078537 A1 * | 5/2014 |
| | (Continued) | |

OTHER PUBLICATIONS

International Search Report (PCT/US17/38332) dated Dec. 28, 2017.
(Continued)

*Primary Examiner* — Peter A Salamon
(74) *Attorney, Agent, or Firm* — Dentsply Sirona Inc.

(57) ABSTRACT

This invention designs and builds multiple layers (two layers or more) of various dental devices, specifically denture base or denture, where printed multiple layered denture base with teeth cavities to receive artificial denture tooth materials to form final dental devices, such as partial and full dentures. It can also print denture teeth. This invention also designs and prints multiple layers (two layers or more) of denture base with artificial denture teeth to form final dental devices, such as partial and full dentures. A method for manufacturing a layered denture is provided. The invention provides a multiple layered denture base materials for printing a denture base. The invention also provides a multiple layered denture tooth materials for printing artificial denture teeth. Highly shape adjustable or shape memory polymer layer(s) may be used in these multiple layered denture base forms. Different layer of material has different mechanical and physical properties to meet different need, which provide added benefits to the patients, dental professional and dental laboratory.

11 Claims, 6 Drawing Sheets

(51) Int. Cl.
*C08G 18/73* (2006.01)
*C08G 18/75* (2006.01)
*C08G 18/10* (2006.01)
*C08G 18/28* (2006.01)
*C08L 75/04* (2006.01)
*B33Y 70/00* (2015.01)
*B33Y 80/00* (2015.01)

(52) U.S. Cl.
CPC ............... *A61K 6/08* (2013.01); *C08G 18/10* (2013.01); *C08G 18/2805* (2013.01); *C08G 18/73* (2013.01); *C08G 18/755* (2013.01); *C08L 75/04* (2013.01); *A61C 2202/01* (2013.01); *B33Y 70/00* (2014.12); *B33Y 80/00* (2014.12)

(56) References Cited

U.S. PATENT DOCUMENTS

| | | | |
|---|---|---|---|
| 5,204,055 A | 4/1993 | Sachs | |
| 5,506,607 A | 4/1996 | Sanders | |
| 5,740,051 A | 4/1998 | Sanders | |
| 5,902,441 A | 5/1999 | Bredt | |
| 6,270,335 B2 * | 8/2001 | Leyden | B29C 41/12 425/375 |
| 6,322,728 B1 * | 11/2001 | Brodkin | A61C 13/0003 264/113 |
| 6,353,041 B1 * | 3/2002 | Qian | A61K 6/0038 433/228.1 |
| 6,472,454 B1 * | 10/2002 | Qian | A61K 6/0038 433/228.1 |
| 6,592,369 B2 * | 7/2003 | Sun | A61K 6/083 433/167 |
| 6,660,209 B2 | 12/2003 | Leyden | |
| 6,921,500 B1 * | 7/2005 | Feenstra | A61C 13/0004 264/19 |
| 6,939,489 B2 * | 9/2005 | Moszner | A61C 13/0004 264/16 |
| 6,955,776 B1 | 10/2005 | Feenstra | |
| 7,175,433 B2 * | 2/2007 | Sun | A61K 6/0017 433/167 |
| 7,189,344 B2 * | 3/2007 | Rheinberger | A61C 13/0003 264/16 |
| 2004/0094058 A1 * | 5/2004 | Kasperchik | C04B 35/624 101/483 |
| 2005/0082710 A1 | 4/2005 | Oriakhi | |
| 2009/0176194 A1 * | 7/2009 | Qian | A61K 6/0023 433/228.1 |
| 2010/0041786 A1 * | 2/2010 | Qian | A61K 6/083 522/154 |

FOREIGN PATENT DOCUMENTS

| | | |
|---|---|---|
| WO | 2014172716 A1 | 10/2014 |
| WO | 2016182444 A1 | 11/2016 |

OTHER PUBLICATIONS

International Preliminary Report (PCT/US17/38332) dated Jun. 20, 2017.

Written Opinion of the International Search Report (PCT/US17/38332) dated Jun. 20, 2017.

* cited by examiner

THREE-DIMENSIONAL FABRICATING MATERIAL SYSTEMS AND METHODS FOR PRODUCING LAYERED DENTAL PRODUCTS

CROSS-REFERENCE TO RELATED APPLICATIONS

This patent application claims the benefit of and priority to U.S. Provisional Application Ser. No. 62/352,320, filed on Jun. 20, 2016, which is herein incorporated by reference for all purposes.

TECHNICAL FIELD

In the present invention, several material systems and methods are used to manufacture the dental device. The use of these material systems by several 3D printing methods can easily prepare multiple layered dental devices. Different layer of material has different mechanical and physical properties to meet different need, which provide added benefits to the patients, dental professional and dental laboratory.

BACKGROUND OF THE INVENTION

The present invention relates generally to rapid prototyping systems, specifically, 3D printing systems for making multiple layered dental devices such as, for example, artificial teeth, dentures, splints, veneers, inlays, onlays, orthodontics, aligners, retainers, copings, frame patterns, crowns and bridges, models, appliances and the like. More particularly, it is related to the use of ink-jet, fused deposition modeling (FDM), selective laser sintering (SLS), stereolithography (SLA), digital light processing (DLP) or their combinations to build-up the dental devices as three-dimensional objects from many material systems and novel resin systems of this invention. Ink-jet printing system dispenses materials through ink-jet printing head to form 3D object, which harden by cooling, polymerization, and light irradiation. FDM extrudes thermoplastic materials throughout nozzle to build 3D object. SLS uses laser as power source to sinter powdered materials to form solid objects. SLA using laser beam traces out the shape of each layer and hardens the photosensitive resin in a vat (reservoir or bath). DLP system builds three-dimensional objects by using the Digital Light Processor (DLP) projector to project sequential voxel planes into liquid resin, which then caused the liquid resin to cure.

In general, rapid prototyping refers to a conventional manufacturing process used to make parts, wherein the part is built on a layer-by-layer basis using layers of hardening material. Per this technology, the part to be manufactured is considered a series of discrete cross-sectional regions which, when combined together, make-up a three-dimensional structure. The building-up of a part layer-by-layer is very different than conventional machining technologies, where metal or plastic pieces are cut and drilled to a desired shape. In rapid prototyping technology, the parts are produced directly from computer-aided design (CAD) or other digital images. Software is used to slice the digital image into thin cross-sectional layers. Then, the part is constructed by placing layers of plastic or other hardening material on top of each other. There are many different techniques that can be used to combine the layers of structural material. A final curing step may be required to fully cure the layers of material for some of the techniques. The application of sealer may be needed to form a dense 3D objects for some of the techniques, such as inkjet printing of a powder bed or FDM. Additional milling may be added to some of the techniques too.

Ink-jet printing technology is a rapid prototyping method that can be used to fabricate the three-dimensional object. In one well known ink-jet printing method that was developed at Massachusetts Institute of Technology, as described in Sachs et al., U.S. Pat. No. 5,204,055, printer heads are used to discharge a binder material onto a layer of powder particulate in a powder bed. The powdered layer corresponds to a digitally superposed section of the object that will be produced. The binder causes the powder particles to fuse together in selected areas. This results in a fused cross-sectional segment of the object being formed on the platform. The steps are repeated for each new layer until the desired object is achieved. In a final step, a laser beam scans the object causing the powdered layers to sinter and fuse together if needed. In another ink-jet printing process, as described in Sanders, U.S. Pat. Nos. 5,506,607 and 5,740,051, a low-melting thermoplastic material is dispensed through one ink-jet printing head to form a three-dimensional object. A second ink-jet printer head dispenses wax material or other supporting material to form supports for the three-dimensional object. After the object has been produced, the wax supports are removed, and the object is finished as needed. MultiJet printers, such as, the high-quality PolyJet and MultiJet 3D printing processes use a UV light to crosslink a photopolymer. However, rather than scanning a laser to cure layers, a printer jet sprays tiny droplets of the photopolymer (similar to ink in an inkjet printer) in the shape of the first layer. The UV lamp attached to the printer head crosslinks the polymer and locks the shape of the layer in place. The build platform then descends by one layer thickness, and more material is deposited directly onto the previous layer. Triple-jetting technology (PolyJet) used in Stratasys Objet 500 Connex3, is the most advanced method of PolyJet 3D printing. This technology performs precise printing with three materials and thus makes three-color mixing possible.

Fused deposition modeling (FDM) technology was developed and implemented at first time by Scott Crump, Stratasys Ltd. founder, in 1980s. What is good about this technology that all parts printed with FDM can go in high-performance and engineering-grade thermoplastic. FDM is the only 3D printing technology that builds parts with production-grade thermoplastics, so things printed are of excellent mechanical, thermal and chemical qualities. 3D printing machines that use FDM Technology build objects layer by layer from the bottom up by heating and extruding thermoplastic filament. Along to thermoplastic a printer can extrude support materials as well. Then the printer heats thermoplastic till its melting point and extrudes it throughout nozzle to a build platform. To support upper layer the printer may place underneath special material that can be dissolved after printing is completed. When the thin layer of plastic binds to the layer beneath it, it cools down and hardens. Once the layer is finished, the base is lowered to start building of the next layer. This technology is considered to be simple-to-use and environment-friendly. Different kind of thermoplastics can be used to print dental objects.

Selective Laser Sintering (SLS) is a technique that uses laser as power source to form solid 3D objects. This technique was developed by Carl Deckard, a student of Texas University, and his professor Joe Beaman in 1980s. The main difference between SLS and SLA is that it uses powdered material in the vat instead of liquid resin as stereolithography does. Unlike some other additive manufacturing processes, such as stereolithography (SLA) and fused deposition modeling (FDM), SLS doesn't need to use any support structures as the object being printed is constantly surrounded by unsintered powder. Due to wide variety of materials that can be used with this type of 3D printer the technology is very popular for 3D printing customized products. SLS requires the use of high-powered lasers, which makes the printer to be very expensive. Extensive surface finishing is required for dental objects made with this process.

SLA 3D printing method was patented by Charles Hull, co-founder of 3D Systems, Inc. in 1986, which converts liquid plastic into solid 3D objects. SLA 3D printers work with excess of liquid resin that hardens and forms into solid object by irradiation. Parts built usually have smooth surfaces but its quality very depends on the quality of SLA machine used. After plastic hardens a platform of the printer drops down (top down printer) or move up (bottom up printer) in the tank a fraction of a millimeter and laser forms the next layer until printing is completed. Once all layers are printed the object needs to be rinsed with a solvent and then placed in a post-cure oven to finish processing.

Digital Light Processing is another 3D Printing process very similar to stereolithography. The DLP technology was created in 1987 by Larry Hornbeck of Texas Instruments and became very popular in Projectors production. It uses digital micro mirrors laid out on a semiconductor chip. 3D inkjet, DLP and SLA all works with photopolymers. The difference between SLA and DLP processes is a different light source. DLP method projects sequential voxel planes into liquid resin, which then caused the liquid resin to cure. The material to be used for printing is liquid resin that is placed in the transparent resin container. The resin hardens quickly when affected by irradiation of light. The printing speed is pretty impressive, especially with Carbon3D's CLIP (Continuous Liquid Interface Production) technology. The layer of hardened material can be created with such printer in a few seconds. When the layer is finished, it's moved up and the next layer is started to be worked on. CLIP technology balances light and oxygen to eliminate the mechanical steps and layers that are the standard DLP process step and allow the production of commercial quality objects at high speed.

This invention provides digital dental devices using computer-aided 3D printing methods as mentioned above. In particular, it is related to designing and manufacturing two or multiple layered dental devices or dental prostheses, such as partial, full dentures or other prosthetic devices, specifically, printing partial, full dentures, surgical guides, nightguards, flippers, splints, orthodontic devices, aligners, retainers, crowns, bridges, partial or full denture bases using computer aided design and printing methods.

Dental devices, specifically for example, denture base and denture tooth should exhibit certain desirable physical characteristics to be suitable for use and offer desirable benefits to patients. They should be dimensional stable for effective functioning, sufficient strength to withstand masticating stresses and resistant to abrasion and chipping during use. They also should be durable and stable to solvents, foods, water, cold and hot and maintain esthetics without discoloration. In addition, they should be esthetics to mimic natural dentition and gum with esthetically acceptable color, i.e., close to that of natural dentition and gum. The denture base and denture tooth should not wear or deform out of occlusion, and denture base should be capable of being bonded firmly to artificial teeth. They should also be adjustable to ordinary means of physical shaping, grinding, and polishing. Denture base and denture tooth materials should be stable without discoloration and provide consistent handling properties during their shelf life. Denture fabricated from denture base and denture tooth materials should provide function, comfort and fit to the patients. It is desirable that denture base materials are compatible with hard and soft mucosal tissues. So it is desirable that denture base contains at least two different materials with different physical and mechanical properties. It is preferable that denture can be easily adjustable to provide better retention, better occlusal contact and better fit so as to provide better function, comfort and performance for patient. It is also preferable that denture can be locally adjustable while other parts remain unchanged.

Typically, denture bases are methacrylate-based acrylics, thermoplastic based or light curable resin based. Most common denture tooth materials are also methacrylate-based acrylics. In general, methacrylate-based acrylics denture bases and teeth are made out of dough from the blending of PMMA or modified PMMA polymer powders with MMA or modified MMA liquids. Denture teeth are commonly made in a tooth manufacturer. Dental lab typically uses denture teeth and denture base material from manufacturer to make denture for patient. The initial step(s) commonly used in the making a denture by making a final impression of a patient's mouth. A cast (or record base) is made of the final impression of a patient's mouth. Typically the cast is made of plaster. Then wax is shaped into the form of a denture base on the cast of the patient's mouth and artificial teeth are positioned into the denture base shaped wax. The denture base shaped wax with the artificial denture teeth is then positioned in an articulator. The artificial teeth in the denture base shaped wax are then articulated. The articulated denture base shaped wax with the artificial teeth is then positioned in a flask. The volume of the flask is filled with hardenable investment material, such as plaster. After the investment material hardens the wax is eliminated, for example by heating the flask in boiling water, leaving the artificial teeth supported by the investment material and a denture base shaped mold cavity within the investment material. After a thorough cleansing of the mold cavity, a denture base material is introduced into the mold cavity. The denture base material then hardens to form a denture. The process to make a denture is long, time-consuming and labor intensive.

Preparation of full and partial dentures typically requires several dental office visits by each patient. The visits include labor intensive processes such as the construction of the base-plate and occlusion rims, wax try-in, invest the wax-up, wax removal and compression packing or pouring of denture base acrylic as described early. This traditional method typically resulted in a denture base containing homogeneous denture base material, which supported artificial denture teeth. A method of using light polymerizable wax like material (Eclipse system sold by Dentsply International) reduces the dental office and laboratory visits and the labor involved in making the denture, which provides a process for making a denture, comprising: articulating artificial teeth while supported by polymerizable material, whereby a denture comprising said artificial teeth is provided without forming a mold for making tooth setup volume of a denture base. The process is completed without forming wax and without applying inorganic plaster to the artificial teeth. Multiple layers of denture base materials are possible and are included in the denture base by this method.

Most recently, 3D printing systems have been using to make denture base and denture. Various 3D printing materials are used for 3D printing to make denture base and denture. Using acquired digital data, a 3D printer prints materials to form final denture with denture base and denture teeth made from different materials. A 3D printer may also print material to form desired denture base, where commercially available artificial denture teeth are subsequently placed into printed cavities and bonded to this denture base. Separately, some denture teeth are also printed by a 3D printer and used to place into printed cavities and bonding to the printed denture base. Dentca's 3D Denture Base System scans the impression and builds denture base layer by layer using a stereolithographic laser printer and then bonds plastic teeth and final cures in a light chamber. FDM 3D printing method prints a denture using FDM printer with scanned or CAD data, which extrudes and deposits molten thermoplastic in layers to build denture from bottom up. Each layer of molten thermoplastic material is deposited on top of previous one and flattened slightly by the extrusion head. The layers are fused together to form final denture base.

Even though current 3D printing methods are very promising, there are still no consistently reliable 3D printing methods and materials to replace the current proven and established methods and materials for denture fabrications by dental laboratory technicians. Conventional denture fabrication process incorporates several steps to ensure the accuracy and functionality of each denture. Nevertheless, some of 3D printing methods required complicated process to obtain digital data. The fabricated denture may not fit in patient's mouth and teeth may not occlude correctly, additional adjustment or reline is needed that can be labor intensive and painful process. Unstable bites on the denture will result in a poor fit. Denture may need to be remade that cost time, money and delay the patient care. Excessive grinding of teeth and denture base may be needed to achieve desired occlusion, which will result in the loss of esthetics of both fabricated denture base and artificial denture teeth and require additional finishing and polishing. It also faces the potential of grinding away more wear resistant enamel layers which commonly existed in some of artificial denture teeth and exposed the less wear resistant dentin layer. In order to avoid above issues, manufacturers and labs often make a try-in denture for the patient. After tried-in, adjusted and confirmed, and then duplicated the tried-in denture by printing or other fabrication methods, which adds additional steps back and requires additional office visits.

It is desirable the denture fabricated can be adjusted during final denture try-in to obtain desirable occlusion without the need of excessive of remaking, grinding, finishing and polishing. A denture fabricated where artificial denture teeth can be adjusted is highly desirable, which can avoid the need of additional tried-in step. It is also desirable the denture fabricated can be comfortable fit perfectly into oral cavity with rigid area to support artificial denture teeth and soft or relatively flexible contact surface to mucosal area for comfort and fit. Typically, denture bases are PMMA based acrylics. However, PMMA and MMA based denture bases have the disadvantage of being subject to brittle fracture due to the nature of PMMA. Rubber impact modified PMMA acrylics were used to improve their fracture toughness and impact strength. Full denture is typically formed from a rigid material since it is needed to support the artificial teeth chewing function without any movement during action. Flexible partial dentures, typically made of flexible thermoplastics, such as Nylon 12, acetal resin, etc. are being commonly used for patients, which provide comfort due to their compliance and flexibility. The use of clasps enables to stabilize the artificial denture teeth in place. The resilience and flexibility of these denture bases are limited due to the need to support artificial denture teeth. Significantly improved resiliency of tissue contact surface is desirable without compromising the artificial denture teeth stability during mastication. It is desirable to have a denture that provides a rigid ridge to support artificial denture teeth in position and resilient and flexible contact layer/area to patient's soft mucosal area for comfort and fit, which is more compatible to patient's oral cavity containing rigid ridge area and soft mucosal area. It is also desirable to have a partial denture that provides a rigid ridge to support artificial denture teeth in position, toughening clasps to stabilize the partial denture in place, and resilient and flexible contact layer/area to patient's soft mucosal area for comfort and fit, which is more compatible to patient's oral cavity containing remaining teeth, rigid ridge area and soft mucosal area. Common practice to improve the patient's comfort and fit is to reline a denture with a soft reline material, which requires additional labor intensive step. It is desirable to provide an integrated denture incorporating a soft layer onto rigid denture base or having two or more areas that offer different performances including a tooth adjustable area. In addition, it is desirable that the contact surface of denture to mucosal area can be adjusted easily to get better fit. It is also desirable that the contact surface of denture to mucosal area can be adjusted and re-adjusted as needed, such as the need due to the ridge resorption over time. An adjustable polymer layer or a shape memory polymer is especially desirable to be used here. When digital intraoral scan is used for the fabrication of denture or denture base, a digital designed tissue side of denture may not perfectly fit to the oral cavity of the patient due to intraoral scanning involving soft tissues and an adjustable polymer layer or a shape memory polymer layer at tissue side allows the denture to be easily adjusted to fit the oral cavity of the patient to get the best fit and comfort. It is also desirable to have a denture, where limited tooth adjustment can be easily achieved. Denture base material around denture teeth can be easily adjusted at elevated temperature or other conditions is preferred.

Even though this invention referred mainly to denture, denture base and teeth, the printing methods and materials of this invention are not limited to the printing of denture, denture teeth or denture base, they can be used to print various dental devices. Their shades can be formed from clear to highly pigmented shade. For example, a multiple layered nightguard can be printed, where the hard and wear resistant top surface layer can effectively withstand wearing and grinding while flexible or resilient side or not occlusal contact part in nightguard can provide comfort, retention and easy insertion and easy removal for the patient. The denture base or denture tooth materials mentioned in this invention can be easily referred as dental materials, such as restorative materials, night guard materials, retainer materials, or aligner materials, etc.

Leyden et al., U.S. Pat. Nos. 6,660,209 and 6,270,335 disclose an ink-jet printing method using commercial print heads having multiple orifices (jets) to selectively fire droplets of hot melt, radiation-curable material onto a substrate. Each orifice can be equipped with a piezoelectric element that causes a pressure wave to propagate through the material when electric current is applied. The print head moves along a scan path selectively depositing the flowable material onto the substrate. In a subsequent step, light radiation is used to cure the material.

Yamane et al., U.S. Pat. No. 5,059,266 discloses an ink-jetting method, whereby a photosetting or thermosetting resin is jetted along a flight passage of the material to a stage to thereby laminate the material on the stage, changing at least one of a jetting direction of the material along the flight passage and a jetting amount of the material, thereby controlling a jetting operation of the material, and exposing the laminated material to light to cure the material, thereby forming the article.

Bredt et al., U.S. Pat. No. 5,902,441 describes another ink-jet printing method, which involves applying a layer of powder particles containing an activatable adhesive onto a flat surface that can be indexed downward. The ink-jet printer introduces an activating fluid onto to the layer of particles in a predetermined pattern. The fluid activates the adhesive in the mixture, causing the particles to adhere together in an essentially solid layer. After the first cross-sectional portion of the article is formed, the movable surface can be indexed downward. Successive layers of the mixture of particles are applied in the same manner to form the desired article.

Oriakhi et al. discloses in US Patent Application Publication No. US 2005/0082710 an ink-jet printing method, wherein a particulate blend of reactive glass ionomer particulates, cross-linkable polyacid particulates including polyvinyl pyrrolidone-co-polyacrylic acid, and nanocomposites is spread in a fabrication bin. An ink-jet printer applies an aqueous phase binder onto a predetermined area of the particulate blend to form hydrated cement. A glass-ionomer chemical reaction causes the hydrated cement to harden.

Kapserchik et al. discloses in US Patent Application Publication No. US 2004/0094058 an ink-jet printing system using acid-base cements. Layers of powder particulate are deposited on a flat surface. The powders include a base such as a metal oxide or an aluminosilicate glass, a polymeric acid or other acid. The ink-jet printer dispenses an aqueous binder. The basic powder interacts with the acid in the presence of water, causing the formation of an ionically cross-linked hydrogel salt. Formation of the cross-linked hydrogel causes setting of the mixture.

More particularly, ink-jet printing methods for making three-dimensional dental products have been developed and are described in the patent literature. For example, Moszner et al., U.S. Pat. No. 6,939,489 discloses a process for fabricating three-dimensional dental form pieces for dental restoration and replacement parts using three-dimensional plotting technology. The object is produced in a layered manner by the cutting away of micro drops or micro cords discharged from nozzles in the three-dimensional plotter. The discharged material can be hardened by a variety of mechanisms depending upon the type of material used. This includes cooling of melted material, polycondensation, polyaddition, or thermal-curing, and light radiation. In the '489 Patent, the three-dimensional plotting technology is described as being different than conventional rapid prototyping (selective laser sintering, 3D printing, and stereolithography).

Rheinberger et al., U.S. Pat. No. 7,189,344 discloses a process for producing three-dimensional dental restorative parts, such as full or partial dental prosthesis, using ink-jet printers that are used in the ink-jet printing methods developed by MIT as described above. The process involves spraying a polymerizable material onto a base support in a layer-by-layer manner. Each layer of material is polymerized by a light source prior to the application of the next layer. The polymerizable material is described as being wax-like having up to 70% by weight of at least one of a polymerizable monomer and oligomer; from 0.01 to 10% by weight of a polymerization initiator; and at least 20% by weight of a mixture having a selected one of a wax-like and flowable monomer and a color pigment.

Feenstra, U.S. Pat. Nos. 6, 921,500 and 6,955,776 disclose an ink-jet printing process for making dental elements such as crowns using a liquid binder and powder bed. The element is produced by applying successive layers of powder and discharging the liquid binder onto the layers using an ink-jet printer. The binder preferably includes nanomeric, inorganic solid particles having polymerizable and/or poly-condensable organic groups at their surface. After the binder has been applied to the last layer of powder, any excess, unbound powder is removed. Then, the powdered layers are sintered by heating to a temperature in the range of about 400 to 800° C. The sintering step is performed so that only necks between the powder particles are formed. The resulting sintered dental element is infiltrated by a second phase material, such as glass-ceramic or polymer, which melts at a lower temperature than the material of the dental element. This reduces the porosity of the dental element.

Bordkin et al., U.S. Pat. No. 6,322,728 discloses an ink-jet printing process for making dental restorations by printing a binder into layers of powder. The process involves depositing a layer of ceramic or composite powder material onto a powder bed. The design of the restoration is based on a CAD representation. A binding material is applied onto the ceramic or composite layer. This application of powder/binder material is repeated several times to produce the desired shape of the restoration. After the layering process is completed, the structure is cured to further promote binding of the particles.

The present invention provides novel high strength/toughness, resilient or high toughness liquid resin/composite systems for fabricating three-dimensional dental devices using the Inkjet, Digital Light Processor (DLP) projectors or stereolithography. This invention can also use many commercially available materials, such as polymerizable resins, thermoplastic materials, shape memory polymers, etc., their combinations and their combinations with liquid resin/composite systems of this invention and several early inventions of present inventor(s) for fabricating three-dimensional dental devices using the Inkjet, FDM, DLP, SLS, SLA or their combinations. Although the Inkjet, DLP or SLA method and high strength/toughness, resilient or high toughness materials are described primarily herein as being used to make a layered dental prosthesis, such as splint, aligner, full and partial denture, denture base and artificial teeth, etc., it should be understood that this is for illustration purposes only. The inkjet, DLP method or SLA method using high strength/toughness, resilient or high toughness materials can be used to make any dental device such as, for example, artificial teeth, dentures, orthodontics, splints, veneers, inlays, onlays, copings, frame patterns, retainers, aligners, flippers, night guards, sport guards, crowns and bridges and the like. We have provided a general description of these methods using high strength/toughness, resilient or high toughness material systems as follows. (A more detailed description of the methods and high strength/toughness, resilient, or high toughness materials used to make the dental devices is set forth below.)

In this method, a polymerizable liquid resin material or heated resin material as a liquid is loaded into a resin bath of a 3D printer based on a DLP method, SLA method or a combination of DLP and SLA. In the case of using DLP method, it builds 3D objects by projecting sequential voxel planes into liquid resin (or heated liquid resin), which then polymerizes it to solid. Successive layers of polymerized material are added in this manner until the device is completely fabricated. Multiple light (or laser) sources may be used with these methods. Once first object was built with successive layers of first polymerized material, subsequent successive layers of second polymerized material may be added to first polymerized object by these methods, which typically require the projecting sequential voxel planes into liquid resin (or heated liquid resin) from top down or tilted angle. Similarly, additional polymerized materials can be built on above objects having two or more polymerized materials to form final two or more layered device. Then the device, for example, a denture, is washed, finished and fully final cured as needed. The fully cured and polished denture is now ready to be used by the patient. In the case of two layered aligner or splint, two clear vats of polymerizable liquid resin materials might be used and built up the devices layer by layer. Moreover, two or more parts may be printed out separately with different materials and then bonded them together to form final objects (or dental devices). Printed out different material layers (parts) may also be finally cured together to form layered objects (or dental devices).

SUMMARY OF THE INVENTION

It is an object of the invention to provide multiple dental materials for 3D printing a multiple layered dental device.

It is an object of the invention to provide a 3D printing process for making a multiple layered dental device.

It is an object of the invention to provide multiple dental materials for 3D printing a multiple layered denture base or denture.

It is an object of the invention to provide a 3D printing process for making a multiple layered dental device, such as denture base or denture, comprising: printing thin layer by thin layer of at least one polymerizable denture base materials at specific location(s) and curing them thin layer by thin layer, printing additional layers of polymerizable denture base and denture tooth materials (at least one) at specific locations and curing them thin layer by thin layer.

It is an object of the invention to provide an inkjet 3D printing process for making a multiple layered dental device, such as denture base or denture.

It is an object of the invention to provide a DLP based 3D printing process for making a multiple layered dental device, such as denture base or denture.

It is an object of the invention to provide a stereolithography based 3D printing process for making a multiple layered dental device, such as denture base or denture.

It is an object of the invention to provide a DLP and stereolithography based 3D printing process for making a multiple layered dental device, such as denture base or denture.

It is an object of the invention to provide a powder bed inkjet and stereolithography based 3D printing process for making a multiple layered dental device, such as denture base or denture.

It is an object of the invention to provide a 3D printing process for making a multiple layered dental device, such as denture base or denture, with different printing process for different layer.

It is an object of the invention to provide a 3D printing process for making a multiple layered dental device, such as a denture base or denture, comprising: printing at least two layers of different polymerizable denture base materials and denture tooth material(s) thin layer by thin layer, and then final cure as needed.

It is an object of the invention to provide a 3D printing process for making a multiple layered dental device, such as a denture base or denture, comprising: printing at least two layers of different polymerizable denture base materials and denture tooth material(s) thin layer by thin layer, adding additional layers of polymerizable denture tooth materials (at least one layer) thin layer by thin layer and then final cure as needed.

It is an object of the invention to provide a 3D printing process for making a multiple layered dental device, such as a denture base, comprising: 3D printing first layer of polymerizable denture base material thin layer by thin layer first, and then 3D printing second layer of polymerizable denture base material thin layer by thin layer to form second layer of denture base, adding additional layers of polymerizable denture base materials thin layer by thin layer as needed and then final curing them together as needed.

It is an object of the invention to provide a 3D printing process for making a multiple layered dental device, such as a denture, comprising: 3D printing first layer of polymerizable denture tooth material thin layer by thin layer first, and then 3D printing second layer of polymerizable denture tooth material thin layer by thin layer to form second layer of denture tooth, adding additional layers of polymerizable denture tooth materials thin layer by thin layer as needed, and then adding additional layers of polymerizable denture base materials (at least two layers) thin layer by thin layer and then final curing them together as needed.

It is an object of the invention to provide a shaded sealer to locally apply on dental device, such as a denture so as to obtain desired shades and esthetics.

It is an object of the invention to provide a 3D printing process for making a multiple layered dental device, such as a denture base, comprising: printing first layer and second layer of polymerizable denture base materials separately, and then bonding them together.

It is an object of the invention to provide a 3D printing process for making a multiple layered dental device, such as a denture base, comprising: printing first layer, second layer and any additional layer of polymerizable denture base materials separately, and then bonding them together.

It is an object of the invention to provide a 3D printing process for making a multiple layered dental device, such as a denture, comprising: printing first layer and second layer of polymerizable denture base materials and denture tooth material separately, and then bonding them together.

It is an object of the invention to provide a 3D printing process for making a multiple layered dental device, such as a denture, comprising: printing multiple layered polymerizable denture base materials and multiple layered denture tooth materials separately, and then bonding them together.

It is an object of the invention to provide a 3D printing process for making a multiple layered dental device, such as a denture, comprising: printing multiple layered polymerizable denture base materials to form a denture base and printing multiple layered denture tooth materials to form denture teeth, and then bonding them together.

It is an object of the invention to provide a 3D printing process for making a multiple layered dental device, such as a denture, comprising: printing multiple layered polymerizable denture base materials to form a denture base, and then bonding to denture teeth to form final denture.

It is an object of the invention to provide a denture (or denture base) having different shades and hues at different layers and different spots.

It is an object of the invention to provide a multiple layered denture (or denture base) having different shades and hues at different layers and different spots.

It is an object of the invention to provide a denture (or denture base) having different layer materials with different mechanical and physical properties.

It is an object of the invention to provide a denture (or denture base) containing different layer materials ranged from resilient materials with low Tg, to flexible materials and rigid materials with high Tg.

It is an object of the invention to make a multiple layered denture base, where the different layers of materials can be uncured, partially cured or fully cured.

It is an object of the invention to make a multiple layered denture base, where the different layers of materials have different mechanical and physical properties.

It is an object of the invention to provide a multiple layered denture base, where the denture base materials around denture teeth area of printed denture from this block can be adjusted while the rest of denture and tissue side remain shape stable at elevated temperature up to 100° C.

It is an object of the invention to provide a multiple layered denture base, where the denture base materials around denture teeth area of printed denture is shape stable while the rest of denture and tissue side are adjustable at elevated temperature up to 100° C.

It is an object of the invention to provide a multiple layered denture base, where the denture base materials around denture teeth area and tissue side area of printed denture can be adjustable while the rest of denture is shape stable at elevated temperature up to 100° C.

It is an object of the invention to make a multiple layered dental device, where the different layers of materials can be uncured, partially cured or fully cured.

It is an object of the invention to make a multiple layered dental device, where the different layers of materials have different mechanical and physical properties.

It is an object of the invention to provide a multiple layered dental device, where the top contact surface is highly wear resistance and shape stable while the side or area other than contact surface layer is highly adjustable at adjustable condition.

It is an object of the invention to provide a multiple layered dental device, where the top contact surface is highly adjustable while the side or area below other than contact surface layer is shape stable at adjustable condition.

DETAILED DESCRIPTION OF THE INVENTION

This invention designs and prints multiple layers (two layers or more) of various 3D objects, such as dental devices, specifically denture base, splints, aligners, retainers, partial and full dentures, etc. A method for manufacturing a layered dental device, such as denture is provided. The invention prints a multiple layered 3D objects. The invention prints a multiple layered dental device. The invention prints a multiple layered denture base. The invention also prints a multiple layered denture. Highly shape adjustable, resilient or shape memory polymer layer(s) may be used in these multiple layered dental devices. Different layer of material has different mechanical and physical properties to meet different need, which provide added benefits to the patients, dental professional and dental laboratory.

Figure 1A:
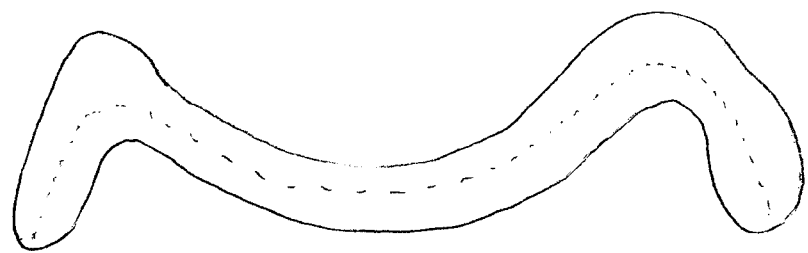
FIG. 1A is seen a schematic cross-sectional view of a denture base with two layered denture base materials.
Figure 1B:
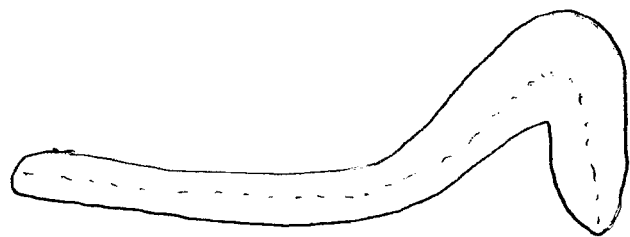
FIG. 1B is a schematic side cross-sectional view of a denture base comprising of two layers.
Figure 1C:
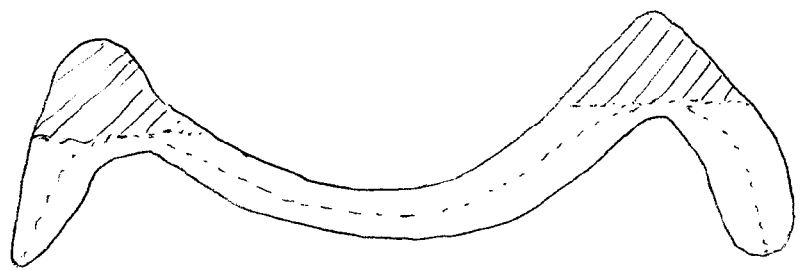
FIG. 1C is a schematic cross-sectional view of a denture base comprising of three layers.
Figure 1D:
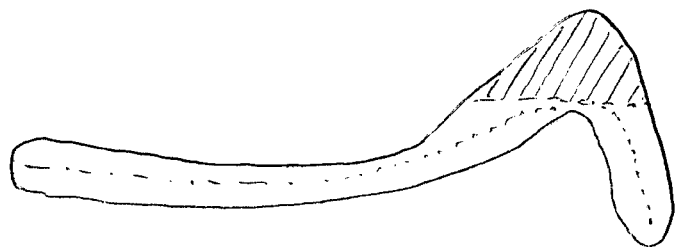
FIG. 1D is another schematic side cross-sectional view of a denture base comprising of three layers.
Figure 2A:
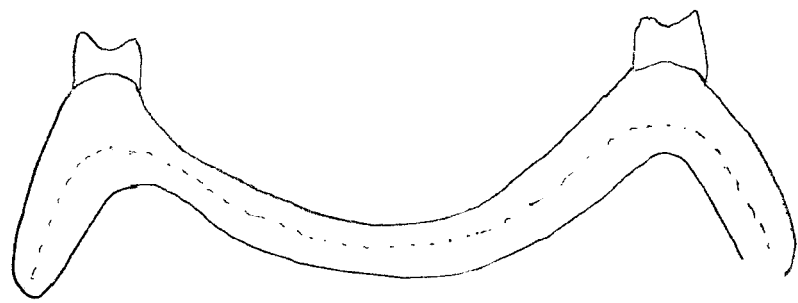
FIG. 2A is seen a schematic cross-sectional view of a multiple layered denture containing two shaded layers of denture base and denture tooth with at least one layer shaded material(s).
Figure 2B:
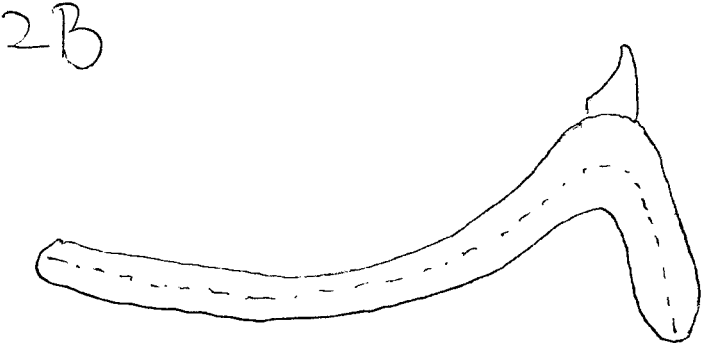
FIG. 2B is seen a schematic side cross-sectional view of a multiple layered denture containing two shaded layers of denture base and denture tooth with at least one layer shaded material(s).
Figure 2C:
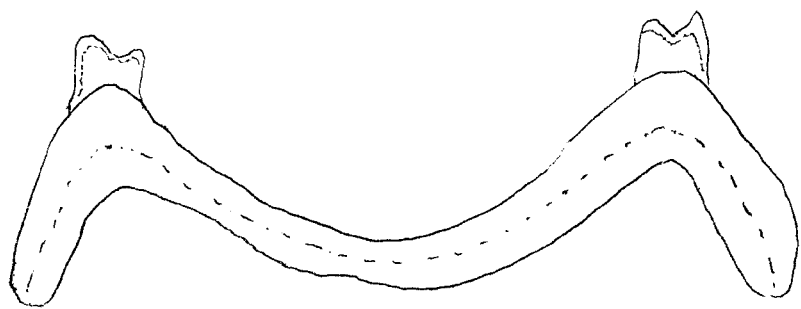
FIG. 2C is a schematic cross-sectional view of a multiple layered denture containing two shaded layers of denture base and two shaded layers of denture tooth materials.
Figure 2D:
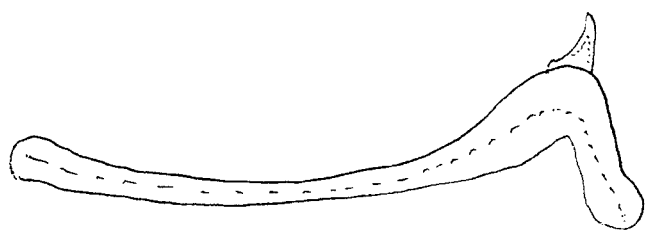
FIG. 2D is another schematic side cross-sectional view of a multiple layered denture containing two shaded layers of denture base and two shaded layers of denture tooth materials.
Figure 2E:
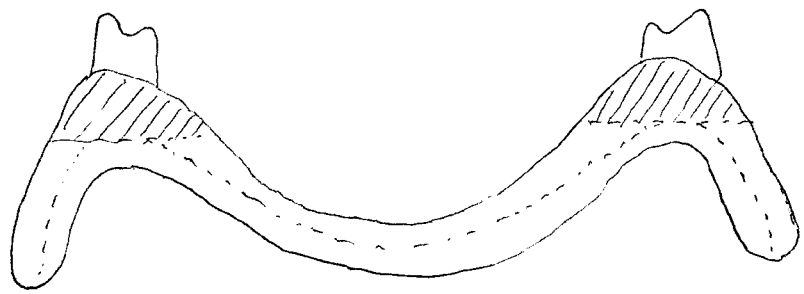
FIG. 2E is seen a schematic cross-sectional view of a multiple layered denture containing three layers shaded denture base and denture tooth with at least one layer shaded material(s).
Figure 2F:
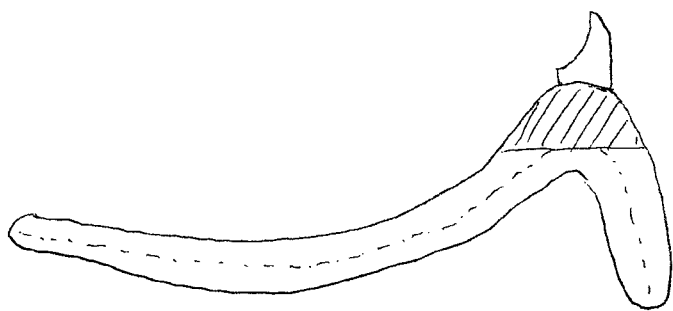
FIG. 2F is seen a schematic side cross-sectional view of a multiple layered denture containing three layers shaded denture base and denture tooth with at least one layer shaded material(s).
Figure 2G:
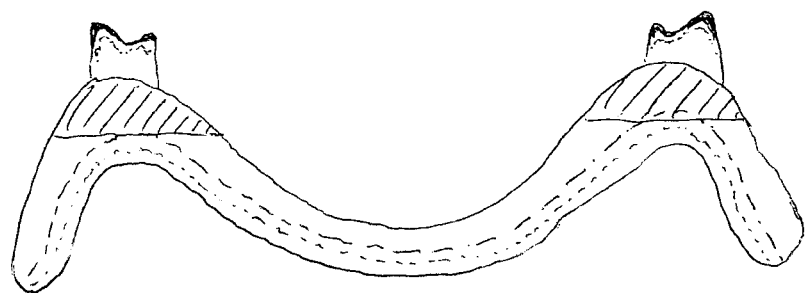
FIG. 2G is seen a schematic cross-sectional view of a multiple layered denture containing multiple shaded layers of denture base and multiple shaded layers of denture tooth.
Figure 2H:
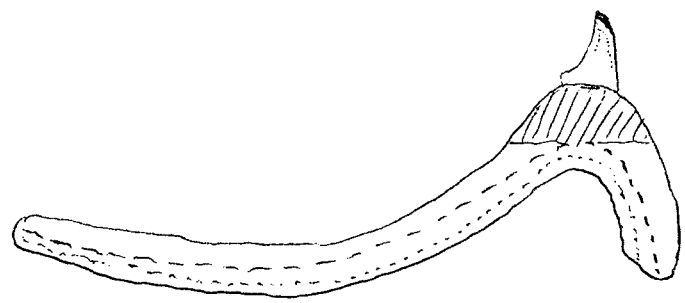
FIG. 2H is seen a schematic side cross-sectional view of a multiple layered denture containing multiple shaded layers of denture base and multiple shaded layers of denture tooth.

The invention is now described with more particular reference to FIGS. 1A through 2H. With particular reference to FIG. 1A is seen a schematic cross-sectional view of a two layered denture base. Two layers of denture base materials may not have uniform thickness. FIG. 1B is another schematic side cross-sectional view of a denture base comprising of two layers. FIG. 1C is a schematic cross-sectional view of a denture base comprising of three layers. FIG. 1D is another schematic cross-sectional side view of a denture base comprising of three layers as shown in FIG. 1C. Every layer may form at different location according to the need of patient. FIG. 2A is seen a schematic cross-sectional view of a multiple layered denture containing two layer denture base materials and at least one denture tooth material layer(s). FIG. 2B is seen a schematic side cross-sectional view of a multiple layered denture containing two denture base material layers and at least one denture tooth material layer(s). Two layers of denture base materials may not have uniform thickness. Denture teeth may sit on the surface of denture base, substantiate submerged into denture base, in between or integrated connected underneath and/or above denture base. FIG. 2C is a schematic cross-sectional view of a multiple layered denture containing two denture base layers and two cured denture tooth layers. FIG. 2D is another schematic side cross-sectional view of a multiple layered denture containing two denture base layers and two denture tooth layers. FIG. 2E is seen a schematic cross-sectional view of a multiple layered denture containing three denture base layers and at least one denture tooth layer. FIG. 2F is a schematic side cross-sectional view of a denture containing three denture base layers and at least one denture tooth layer. FIGS. 2G and 2H are the schematic cross-sectional and side cross-sectional views of a denture containing multiple layers of denture base and multiple layers of denture tooth. These layers in dentures or denture bases can be formed by various 3D printing methods. The printed out thin layers are formed thin layer by thin layer through solidification upon cooling, polymerization by light irradiation, self-cure or heat cure after mixing from two parts materials to form a multiple layered dental devices from the same and/or different materials. Here thin layers are different from layers in layered objects (or dental devices). Thin layer is formed from printing process using the same material, while the layers in layered dental devices may have different physical appearance or physical characteristics (properties and performances). This invention is mainly related to 3D printing for making multiple layered dental prostheses, such as partial and full dentures, denture bases, splints, retainers, aligners, etc. Dental prostheses can be fully cured, uncured or partially cured. A part of dental prosthesis can be fully or partially cured and a part of dental prosthesis can be partially cured or uncured. Partially cured dental prosthesis can be fully cured by light, heat, the combination of light and heat to form final dental devices, such as dentures, partial dentures, nightguards, retainers, etc. Partially and fully cured or uncured part can be easily adjusted after tried in. Partially cured or uncured part may offer easier adjustment. Layered dental device can be printed together, can be printed out individually and then bonded together or the combination of them. It can also be printed with different methods together, separately and then bonded together or the combination of them.

One of the features of the multiple layered dental prosthesis of this invention is that it contains at least two layers of different materials in this dental device or prosthesis, e.g., two layers of different materials in denture and two layers of different materials in denture base. The different materials may form in several specific areas or arch forms as shown in Figures and far beyond to accommodate different needs for the patients, laboratories and dental professionals. The layers may be substantially parallel to the surface of dental device, may be angled to the surface of dental device, may be substantially or locally vertical to the surface of dental device, may be locally embedded among layers with various forms or they may be substantially arch shaped, full or half elliptical shaped, half-bell shaped, full or half circle shaped, or full or half cup shaped, etc. to the surface of dental device. Additional feature includes at least two layers of different or same materials in this dental device may have at least one shade. The layers may form distinctly interfaces, or may be inter-connected with or without distinct interface. For layered dental devices, the interfaces may form from the blending of the materials of both layers, the interpenetration of both layer materials, the final polymerization of partially or uncured layers together, the polymerization of subsequent layer on partially polymerized layer, the polymerization of subsequent layer on polymerized layer, the formation of melting interface, the formation of intimate contact interface, monomer penetration prior to the polymerization on polymerized layer, the formation of mechanical retention interface, or the use of bonding agent or adhesive between layers. During 3D printing, the dental materials for different layers may flow between them. After the polymerization of the polymerizable dental material, there is no detectable interface in the region of the integral connection of the different layers. In the dental device, such as a denture, the artificial tooth is integrally connected to the denture base, different denture base layers and different tooth layers are integrally connected. The dental device, such as a denture may be formed from denture teeth set directly on top of denture base. The dental device is preferably formed from an artificial tooth having tooth material and a submerged tooth surface. A portion of the tooth material flows through the submerged surface into the adjacent denture base. The adjacent denture base includes denture base material. A portion of the denture base material flows through the submerged surface of the artificial tooth whereby the submerged surface of the tooth is assimilated into the tooth material and the adjacent denture base material to form an integral connection between the artificial tooth and the denture base. The flow of tooth and denture base materials typically occurs during polymerization. When polymerization is complete cross-sections of an artificial tooth integrally connected to a denture base at the position of the pre-flowing tooth surface and the adjacent pre-flowing denture base are without a detectable residue of the pre-flowing tooth surface contacting the denture base material.

Another one of the features of the multiple layered dental prosthesis of this invention is that it contains at least two layers of different materials in this dental device or prosthesis, e.g., denture made from at least two different 3D printing methods, such as FDM and DLP, DLP and SLA, DLP and SLS, FDM and SLS, inkjet and DLP, and many combinations. For example, a DLP printed denture base was subsequently located in SLS printer and tooth layer was formed by SLS method. A DLP printed denture base built from bottom up was subsequently irradiated with laser beam traced from above/tilted angle to build second denture base in a second liquid resin vat and additional denture base layer or denture tooth layer may be added in additional changed liquid resin vat as needed. A FDM printed partial denture frame may be subsequently located in a SLA vat to build first layer of denture base, then a different vat may be used to build second layer of denture base. For DLP or SLA method, multiple shaded or multiple materials denture, denture base or other dental devices can be built from multiple shaded or different polymerizable materials in multiple vats. The different materials may form in several specific areas or arch forms as shown in Figures and far beyond to accommodate different needs for the patients, laboratories and dental professionals. In addition, A FDM printed partial frame, DLP printed shape memory layer and tooth support layer as well as artificial denture teeth may be bonded together and final cured to form a partial denture, where the partial frame is preferable embedded between two denture base layers. Alternatively, partial frame can be milled from a CAD/CAM milling machine or made from conventional laboratory process.

For DLP or SLA printing method, several printable polymerizable materials with different shades and color can be prepared and placed into separate vats (baths). In a case of build a denture, two layered denture base is to build from first denture base shaded bath thin layer by thin layer. Preferable, this first denture base forms a shape adjustable or shape memory polymer layer. This denture base is washed and transferred into a second denture base shaded bath to build second denture base layer thin layer by thin layer, where light beams were irradiated from different angles (might be movable up to 360 degree and might irradiate from up to 360 degree from horizontal to vertical directions) so as to allow the thin layer by thin layer built up on the surface of first shaded denture base. Multiple light sources (or beams) as well as different light sources (or beams) may be used in a single printing unit. If desired, additional denture base layer(s) may be built. Then this can be washed and transferred into dentin shaded bath to build dentin layer on the surface of previous built shapes. If desired, additional dentin layer(s) may be built. After it is washed and transferred into an enamel bath, where an enamel layer is built thin layer by thin layer on the surface of previous built shapes and forms a final denture device with integral teeth on two or more layered denture base. If additional shades are desired, additional layers of different dentin and enamel shades or denture base and characterized denture base shades can be built similarly as described above. Nevertheless, a denture may be built by reversal steps, where teeth or enamel are built first and then denture base. Alternatively, layered denture base may be printed and then bonded to artificial denture teeth.

For inkjet printing method, commercially available process or printer can be used to build a multiple layered dental device, such as denture or denture base, using several different materials for different performances. In a preferred embodiment of the invention, a layer of polymerizable (or polymeric) denture base material was printed to form a first layer of denture base form, which is uncured, partially cured or fully cured to form first layer of denture base at desired location. Subsequently, a second layer of polymerizable (or polymeric) denture base material was printed on top of first layer denture base to form a second denture base layer of denture base form, which is uncured, partially cured or fully cured to form second layer of denture base at desired location. Additional layers might be printed as needed. Alternatively, additional final cure may be applied for this denture base if needed.

In another preferred embodiment of the invention, a layer of polymerizable (or polymeric) denture base material was printed to form a first layer of denture base form, which is uncured, partially cured or fully cured to form first layer of denture base at desired location. Subsequently, a second layer of polymerizable (or polymeric) denture base material was printed on top of first layer denture base to form a second denture base layer of denture base form, which is uncured, partially cured or fully cured to form second layer of denture base at desired location. Then, a first layer of polymerizable (or polymeric) denture tooth material was printed on top of denture base to form a first denture tooth layer on denture base form, which is uncured, partially cured or fully cured to form first layer of denture tooth. Then another layer of polymerizable (or polymeric) denture tooth material was printed on top of first denture tooth layer and denture base to form a second denture tooth layer of denture form, which is uncured, partially cured or fully cured to form second denture tooth layer of denture at desired location. Additional layers might be printed as needed. In addition, additional final cure may be applied for this denture if needed. Nevertheless, a denture may be built by reversal steps, where teeth are built first and then denture base.

In yet another preferred embodiment of the invention, at least two polymerizable denture base materials and at least one polymerizable denture tooth material (including composite) were printed to form a multiple layered denture, which is uncured, partially cured or fully cured. Additional final cure may be applied for this denture. One layer of denture base at the tissue, at denture teeth side or both can be easily adjusted as needed.

In yet another preferred embodiment of the invention, at least two polymeric based denture base materials and at least one polymeric based denture tooth material (including composite) were printed to form a multiple layered denture.

In yet another preferred embodiment of the invention, the combinations of polymerizable and polymeric based at least two denture base materials and at least one denture tooth material (including composite) were printed to form a multiple layered denture.

In yet another preferred embodiment of the invention, a layer of polymerizable (or polymeric) denture tooth material (including composite) was printed to form a first layer of denture tooth form, which is uncured, partially cured or fully cured to form first layer of denture tooth at desired location. Subsequently, a second layer of polymerizable (or polymeric) denture tooth material (including composite) was printed on top of first layer denture tooth to form a second denture tooth layer of denture tooth form, which is uncured, partially cured or fully cured to form second layer of denture tooth at desired location. Additional layers might be printed as needed. Alternatively, additional final cure may be applied for this denture tooth if needed.

In yet another preferred embodiment of the invention, a layer of polymerizable (or polymeric) denture tooth material (including composite) was printed to form a first layer of denture tooth form, which is uncured, partially cured or fully cured to form first layer of denture tooth at desired location. Additional layers might be printed as needed. Subsequently, a first layer of polymerizable (or polymeric) denture base material (including composite) was printed on denture tooth to form a first denture base layer of denture form, which is uncured, partially cured or fully cured to form first layer of denture base at desired location. Then another layer of polymerizable (or polymeric) denture base material (including composite) was printed on top of first denture base layer and denture tooth to form a second denture base layer of denture form, which is uncured, partially cured or fully cured to form second denture base layer of denture at desired location. Additional layers might be printed as needed. Finally, additional final cure may be applied for this denture if needed.

In yet another preferred embodiment of the invention, at least two polymerizable (or polymeric or the combination of polymerizable and polymeric) denture base materials (at least one of them forms shape memory polymeric layer) and at least one polymerizable (or polymeric or the combination of polymerizable and polymeric) denture tooth material (including composite) was printed to form a multiple layered denture, which is uncured, partially cured or fully cured. Additional final cure may be applied for this denture if needed. One layer of denture base at the tissue, at denture teeth side or both can be easily adjusted or reversed repeatedly as needed.

In yet another preferred embodiment of the invention, a layer of shape memory polymeric material (including composite) was printed to form a first layer denture base of denture. Subsequently, a second layer of polymerizable (or polymeric) denture base material (including composite) was printed on top of first layer denture base to form a second denture base layer of denture, which is uncured, partially cured or fully cured to form second layer of denture base at desired location. Additional layers of various denture base materials (including composite) might be applied as needed. Alternatively, additional final cure may be applied for this denture if needed. Nevertheless, a denture may be built by reversal steps, where the polymerizable (or polymeric) denture base layer is built first and then shape memory polymer layer. One layer of denture base at the tissue, or at denture teeth side can be easily adjusted or reversed repeatedly as needed.

In yet another preferred embodiment of the invention, a first layer of denture base is formed from the printing of a layer of shape memory polymeric (or polymerizable) material. Subsequently, a second layer of polymerizable (or polymeric) denture base material was printed on top of first layer denture base to form a second denture base layer of denture, which is uncured, partially cured or fully cured to form second layer of denture base at desired location. Additional layer of polymerizable (or polymeric) denture base material was printed to form another shape memory polymer layer in denture before the tooth layers. Then, a first layer of polymerizable (or polymeric) denture tooth material was printed on top of denture base layers to form a first denture tooth layer of denture, which is uncured, partially cured or fully cured to form first layer of denture tooth material at desired location. Another layer of polymerizable (or polymeric) denture tooth material was printed on top of first denture tooth layer to form a second denture tooth layer of denture, which is uncured, partially cured or fully cured to form second denture tooth layer of denture block at desired location. Additional layers of denture tooth materials might be applied as needed. Alternatively, additional final cure may be applied for this denture. Both the contour of tissue side and the positions of denture teeth of denture can be adjusted repeatedly and independently once heated to a specific temperature or activated since the shape memory polymeric materials at tissue side and around denture teeth have different phase transition temperatures or different phase transition mechanisms.

The invention provides multiple layered integral denture base with different performances for different layers, multiple layered integral artificial teeth with different performances for different layers, as well as multiple layered integral denture base and artificial teeth with different performances for different layers. In a preferred embodiment of the invention the denture base and artificial tooth layers are preferably shaped by a 3D printing method in partially cured, fully cured or uncured stages. The dental devices or prostheses are formed from polymerizable dental materials, polymeric dental materials, dental composite materials, or the combinations of polymeric dental materials, dental composite materials, and polymerizable dental materials. The dental composite materials may be included in polymerizable dental materials or polymeric dental materials. The dental prostheses or parts of dental prostheses are formed from polymerizable dental materials, which may include one or more initiating systems to cause them to harden promptly. These materials may solidify once they are dispensed and cooled down on desired locations, such as those polymeric materials. These materials may solidify by crystallization once they are dispensed and cooled down on desired locations, such as those claimed in U.S. Pat. Nos. 6,592,369 and 7,175,433, etc. The polymerizable materials can be cured by light or heat once they are applied on desired locations. The polymerizable materials can also have two parts, which are in situ mixed upon dispensing and polymerized by chemical reactions to form desired shapes.

After the printing and polymerization of the multiple layered materials, there are the integral connected multiple layered denture base and integral connected artificial teeth that are well bonded to the denture base. The integral connected artificial teeth provide superior tooth retention compared to conventional denture fabrication process. In the dental device, the artificial teeth are integrally connected and bonded to the denture base. Optional, a portion of the tooth material flows through the interface into the adjacent layer of denture base and is integrated connected underneath and/or above denture base. The adjacent denture base includes various denture base materials. A wide range of denture base and artificial tooth materials may be used here to offer various performances. At least a shape memory layer is especially interesting.

Shape memory polymers (SMPs) included in this invention are especially interesting for use in denture base material layers around denture teeth and at the tissue side of denture. SMP can be printed and formed or cured into any "memorized" shape, specifically the formation of the tissue side layer of denture base. Shape memory polymer systems allow the tissue side layer of denture base be adjusted or reversed and readjusted repeatedly to accommodate the changes of oral cavity. It is especially beneficial to digital denture approaches, where the fit and precision of tissue side layer of denture base and the occlusion of denture teeth depend on the digital information obtained. The major drawback of current intraoral scanning technology is to catch precise tissue side impression since it involves soft oral tissues. This approach allows current intraoral scanning technology to be used chairside since the use of shape memory polymer at tissue side allows the material at tissue side to be adjustable without the need of precise digital impression. For example, thermo-responsive shape memory polymers can be heated above transition temperature to achieve desired shape and cooled down to form desired shape to adapt to the oral cavity. If desired, materials can revert back to original shapes. This process can be repeated to achieve the optimum result. Shape adjustable thermoplastic and thermoset polymer systems are also interested to this invention for use in denture base material layers around denture teeth and at the tissue side of denture. For example, these polymers can be adjusted at elevated temperature and cooled to form desired shapes without revert back to original shape. Even though this invention describes the use of polymeric and polymerizable materials to make dentures or denture bases, polymerizable wax-like materials and their variations (e.g., those claimed in U.S. Pat. Nos. 6,592,369 and 7,175,433, etc.) can be used to make uncured denture/denture base or part of uncured denture/denture base. Polymeric materials include many thermoset and thermoplastic materials can be used to make various multiple layered dental prostheses for different dental application, such as epoxies, acrylics, polystyrene and polystyrene based copolymers, PEEK, PEKK, Nylons, ABS, SAN, polycarbonates, vinyl acetate (EVA) and copolymers, polyurethanes, polymethylpentene, cellulose acetate based polymers, polyolefins and copolymers, synthetic elastomers, silicones, PET, PBT, PPO, and many other thermoplastic and crosslinked polymers and copolymers, etc.

Printable Polymeric Materials

A printable polymeric material is used to make the dental products in accordance with the methods of this invention. By the term, "printable" as used herein, it is meant a material can be 3D printed by a 3D printer, such as FDM based, SLS based, inkjet based 3D printer, etc. Many printable polymeric materials are commercially available, such as acrylics, polystyrene and polystyrene based copolymers, PEEK, PEKK, Nylons, ABS, SAN, polycarbonates, vinyl acetate (EVA) and copolymers, polyurethanes, polymethylpentene, cellulose acetate based polymers, polyolefins and copolymers, synthetic elastomers, silicones, PET, PBT, PPO, their copolymers, and many other polymers and copolymers, etc.

Printable Polymerizable Materials

A printable polymerizable material is used to make the dental products in accordance with the methods of this invention. By the term, "printable" as used herein, it is meant a material can be 3D printed by a 3D printer, such SLA based, DLP based, inkjet based 3D printer, etc., which is flowable (fluid) at a temperature below ambient temperature, at ambient temperature and above ambient temperature. Flowable material has a flowable temperature in the range of −30° C. to 140° C. The following components can be used to prepare the printable polymerizable material in accordance with this invention.

Polymerizable Compounds

Polymerizable acrylic compounds that can be used in the compositions of this invention, include, but are not limited to, mono-, di- or poly-acrylates and methacrylates such as methyl acrylate, methyl methacrylate, methacrylic acid, ethyl acrylate, ethyl methacrylate, isopropyl methacrylate, tert-butyl (meth)acrylate, cyclohexyl (meth)acrylate, 4-tert-butylcyclohexyl (meth)acrylate, tetrahydrofurfuryl (meth)acrylate, n-hexyl acrylate, octadecyl (meth)acrylate, isobornyl (meth)acrylate; isobornyl cyclohexyl (meth)acrylate; cyclohexyl (meth)acrylate, trimethylcyclohexyl (meth)acrylate, 2-butyl (meth)acrylate, 2-hydroxy-3-phenoxypropyl acrylate, 2-phenoxyethyl (meth)acrylate, stearyl acrylate, allyl acrylate, isobornyl (meth)acrylate, stearyl (meth)acrylate, phenoxy benzyl (meth)acrylate, o-phenylphenol ethyl (meth)acrylate, tris (2-hydroxy ethyl) isocyanurate diacrylate, the reaction product of octadecyl isocyanate and 2-hydroxyethyl methacrylate, the reaction product of octadecyl isocyanate and caprolactone 2-(methacryloyloxy)ethyl ester, the reaction product of octadecyl isocyanate and 2-hydroxyethyl acrylate; the reaction product of octadecyl isocyanate and hydroxypropyl (meth)acrylate; the reaction product of octadecyl isocyanate and 2-hydroxypropyl 2-(methacryloyloxy)-ethyl phthalate; the reaction product of octadecyl isocyanate and 2-hydroxy-3-phenoxypropyl acrylate; the reaction product of octadecyl isocyanate and glycerol dimethacrylate; the reaction product of octadecyl isocyanate and pentaerythritol triacrylate; the reaction product of cyclohexyl isocyanate and 2-hydroxyethyl (meth)acrylate; the reaction product of benzyl isocyanate and 2-hydroxyethyl (meth)acrylate; 1,14-tetradecanedimethacrylate, dimethylol tricyclodecane diacrylate, glycerol diacrylate, glycerol triacrylate, ethylene glycol diacrylate, diethyleneglycol diacrylate, triethyleneglycol dimethacrylate, tetraethylene glycol di(meth)acrylate, 1,3-propanediol diacrylate, 1,3-propanediol dimethacrylate, trimethylolpropane tri(meth)acrylate, 1,2,4-butanetriol trimethacrylate, 1,4-cyclohexanediol diacrylate, 1,4-cyclohexanediol dimethacrylate, 1,6-hexanediol di(meth)acrylate, pentaerythritol triacrylate, pentaerythritol tetraacrylate, pentaerythritol tetramethacrylate, sorbitol hexacrylate, 2,2-bis[4-(2-hydroxy-3-acryloyloxypropoxy)phenyl]propane; 2,2-bis[4-(2-hydroxy-3-methacryloyloxypropoxy)phenyl]propane (Bis-GMA); tert-butylcycloxyl (meth)acrylate; cyclohexane dimethanol di(meth)acrylate; the reaction product of Bis-GMA and octadecyl isocyanate; the reaction product of Bis-GMA and cyclohexyl isocyanate; 2,2-bis[4-(acryloyloxy-ethoxy)phenyl]propane; 2,2-bis[4-(methacryloyloxy-ethoxy)phenyl]propane (or ethoxylated bisphenol A-dimethacrylate) (EBPADMA); urethane di(meth)acrylate (UDMA), diurethane dimethacrylate (DUDMA), 4,13-dioxo-3,14 dioxa-5,12-diazahexadecane-1,16-diol diacrylate; 4,13-dioxo-3,14 dioxa-5,12-diazahexadecane-1,16-diol dimethacrylate; 4,19-dioxo-3,20 dioxa-5,18-diazahexadecane-1,22-diol diacrylate; 4,19-dioxo-3,20 dioxa-5,18-diazahexadecane-1,22-diol dimethacrylate; the reaction product of trimethyl 1,6-diisocyanatohexane and bisphenol A propoxylate and 2-hydroxyethyl methacrylate (TBDMA); the reaction product of 1,6 diisocyanatohexane and 2-hydroxyethyl methacrylate modified with water (HDIDMA); the reaction product of 1,6 diisocyanatohexane and 2-hydroxyethyl acrylate modified with water (HDIDA); the reaction product of 1,6-diisocyanatohexane, 1,2-decanediol, 1,10-decanediol and 2-hydroxyethyl (meth)acrylate; the reaction product of 1,6-diisocyanatohexane, 3-hydroxy 2,2-dimethylpropyl 3-hydroxy-2,2-dimethyl propionate, 1,10-decanediol and 2-hydroxyethyl (meth)acrylate; the reaction product of 1,6-diisocyanatohexane, 1,10-decanediol and 2-hydroxyethyl (meth)acrylate; the reaction product of 1,6-diisocyanatohexane, 1,2-decanediol, 1,10-decanediol, 3-hydroxy 2,2-dimethylpropyl 3-hydroxy-2,2-dimethyl propionate and 2-hydroxyethyl (meth)acrylate; the reaction product of 1,6-diisocyanatohexane, trimethyl 1,6-diisocyanatohexane, 1,10-decanediol and 2-hydroxyethyl (meth)acrylate; the reaction product of 1,6-diisocyanatohexane, trimethyl 1,6-diisocyanatohexane, 3-hydroxy 2,2-dimethylpropyl 3-hydroxy-2,2-dimethyl propionate, 1,10-decanediol and 2-hydroxyethyl (meth)acrylate; the reaction product of 1,6-diisocyanatohexane, 2,5-dimethyl-2,5-hexanediol and 2-hydroxyethyl (meth)acrylate; the reaction product of 1,6-diisocyanatohexane, 4,4'-isopropylidenedicyclohexanol and 2-hydroxyethyl (meth)acrylate; the reaction product of 1,6-diisocyanatohexane, 1,2-decanediol, 1,10-decanediol, 3-hydroxy 2,2-dimethylpropyl 3-hydroxy-2,2-dimethyl propionate and 2-hydroxyethyl (meth)acrylate; the reaction products of 2-isocyanatoethyl methacrylate and diols; polyurethane dimethacrylate (PUDMA); alkoxylated pentacrythritol tetraacrylate; many urethane (meth)acrylates; urethane di(meth)acrylate derivatives of (isocyanatoalkyl)cyclohexane (e.g., 1,3-bis(isocyanatomethyl)cyclohexane); urethane di(meth)acrylate derivatives of (isocyanatoalkyl)benzene (e.g., 1,3-bis(isocyanate-2-propyl)benzene); polycarbonate dimethacrylate (PCDMA); the bis-acrylates and bis-methacrylates of polyethylene glycols; (meth)acrylate modified silicones; light curable epoxies; epoxy methacrylate (or acrylate), methacrylate (or acrylate) compounds or their combinations.

Compounds, which are useful in this polymerizable dental material of a preferred embodiment of the invention, also include epoxy methacrylate (or acrylate) compounds, or the various combination of epoxy resins, (meth)acrylate resins or epoxy methacrylate (or acrylate) compounds. Methacrylate (or acrylate) compounds can be light polymerized rapidly in a 3 D printer, post cure in an oven or light unit with heat, light or light and heat combination will enhance the polymerization conversion and improve the mechanical properties and performance of cured dental devices. Methacrylate (or acrylate) compounds generate polymerization stress is reduced due to slower polymerized and ring opening epoxy resin system. Epoxy compounds polymerize by ring-opening polymerization shrinks less and generate less polymerization stress due to the increase in excluded free-volume associated with the ring-opening process. Various epoxides or epoxy (meth)acrylates in combination with various diols, such as 1,3-bis(3-glycidyloxypropyl)tetramethyldisiloxane, bisphenol A proxylate diglycidyl ether, bis (3,4-epoxy-6-methylcyclohexylmethyl)adipate, 1,10 decanediol, 1,6-hexanediol, branched diol, aromatic diol, bisphenol A, proxylated bisphenol A, etc. Epoxy compounds polymerized by ring-opening polymerization shrinks less due to the increase in excluded free-volume associated with the ring-opening process; and copolymerizable mixtures of acrylated monomers and acrylated oligomers, and the like.

Polymerization System

Printable polymerizable dental materials compositions of the invention may include various inorganic and organic fillers, glass fillers, pigments, initiators, catalysts, stabilizers, various modifiers, surfactants, antimicrobial agents, antibiofilm agents, UV absorbing additives, thermal color stabilizers, thixotroping agents, plasticizers, rubber impact modifiers, antifungal agents, fibers or their combinations. Preferred stabilizers are butylated hydroxytoluene (BHT) and the methyl ether of hydroquinone (MEHQ), etc. It may also include compounds/filers to introduce radiopaque in the material. Many red fibers may be used to offer the benefits of esthetic appearance, such as the use of short red acetate fibers.

For example, the denture base and artificial tooth materials used here including dental composite materials, which may optionally include one or more additives that can include, without limitation, at least one filler (e.g., fibers, polymers, glass particles or otherwise), initiators, pigments, an inhibitor, or combinations thereof or others.

Polymerization Initiating System

The printable polymerizable dental materials and compositions of this invention may include one or more initiating systems to cause them to harden promptly. Light polymerizable dental compositions or composites preferably include a light sensitizer, for example 2,4,6-trimethylbenzoyldiphenylphosphine oxide, camphorquinone, or methyl benzoin which causes polymerization to be initiated upon exposure to activating wavelengths of light; and/or a reducing compound, for example tertiary amine. Photoinitiators selected from the class of acylphosphine oxides, which include, for example, monoacyl phosphine oxide derivatives, bisacyl phosphine oxide derivatives, and triacyl phosphine oxide derivatives. For example, 2,4,6-trimethylbenzoyl-diphenyl-phosphine oxide (TPO) can be used as the photopolymerization initiator. Cationic polymerization initiators, diaryliodonium and triaryl sulfonium salts, such as 4-octyloxyphenyl-phenyl iodonium hexafluoroantimonate (OPPI), can also be used, which initiates ring opening polymerization as well as volume expansion from phase change to reduce the polymerization shrinkage. Electron-transfer photosensitizers, such as polynuclear aromatic compounds, their substituted analogues, carbazoles, phenothiazines, curcumin, and titanium-complex free radical initiator can also be added. Photoinitiators can be used are not limited to above examples. Polymerizable dental materials of the invention may include two or more initiating systems to cause them to harden promptly at different rates. Light curable polymerizable dental materials or composites preferably include at least two light sensitizers, for example camphorquinone/4-octyloxy-phenyl-phenyl iodonium hexafluoroantimonate (OPPI) and 2,4,6- trimethylbenzoyldiphenylphosphine oxide, which causes polymerization to be initiated upon exposure to activating wavelengths of light through free-radical polymerization and cationic ring opening polymerization at different rates. The polymerization stress generated in the first polymerization is effectively absorbed by second slow polymerized resin system. Preferably, free-radical polymerization generates polymerization stress is significantly reduced due to free flow (or free mobility) of second cationic ring opening polymerization resin, which polymerizes and generates significantly less polymerization stress. Additional polymerization by heat, light or their combination offers much improved physical properties or performances. Additional examples may include at least a light curable initiator and at least a heat cure initiator, at least a self-curable initiator and at least a heat cure initiator, or at least a self-curable initiator and at least a light cure initiator.

A room temperature or heat activating polymerizable denture base or artificial tooth materials are also preferably include a room temperature (chemical) or heat activating catalyst system. Examples of initiators, include, but are not limited to, dibenzoyl peroxide (BPO), dilauroyl peroxide (LPO), t-butylhydroperoxide, cumene hydroperoxide, di-t-butyl peroxide, dicumyl peroxide, acetyl peroxide, 1-benzyl-5-phenylbarbituric acid (PBS), 5-n-butylbarbituric acid (BBS), an organic peroxide and an amine, an amine and a sulfinic acid salt, an acidic compound and an aryl borate, barbituric acid and alkylborane, barbituric acid and alkyl ammonium chloride/copper chloride, 2,2'-azobis-(isobutyronitrile) (AIBN), 2,2'-azobis-(2,4-dimethyl valeronitrile) (ADMV), tert-butyl per-2-ethyhexanoate (t-BPEH), etc. Other initiating components may include, but are not limited to room temperature or heat activating catalyst components (e.g., system) for curing polymerizable materials (e.g., dental materials) of the invention. For example a peroxide capable of producing free radicals when activated by a reducing agent at room temperature or by heating. Room temperature activated polymerization initiating compounds may preferably include the combinations of peroxide and amine, barbituric acid and copper and/or chloride ions. Heat-activated polymerization initiating compounds may be included to provide a heat-curable polymerizable material. The peroxides generate free radicals to initiate polymerization and hardening of the composition at elevated temperature.

In one embodiment, a photoactive agent such as, for example, 2 weight percent of 2,4,6-trimethylbenzoyl-diphenyl-phosphine oxide (TPO) is added to the composition in order to make it light-curable.

Fillers

Preferably, these polymerizable dental materials may include from about 0 to about 95 percent by weight filler particles. More preferably, these materials include from about 0 to about 85 percent by weight filler. Nanocomposites and ceramers may be used to make these composites/dental materials for this invention. The fillers preferably include both organic and inorganic particulate fillers to further reduce polymerization shrinkage, improve wear resistance and modify the mechanical and physical properties. Commercially available light curable resins and composites, heat or cold curable acrylics, resins or composites can also be used here.

Conventional filler materials such as inorganic fillers, which can be naturally-occurring or synthetic, can be added to the printable polymerizable dental material and composition. Such materials include, but are not limited to, silica, titanium dioxide, iron oxides, silicon nitrides, glasses such as calcium, lead, lithium, cerium, tin, zirconium, strontium, barium, and aluminum-based glasses, borosilicate glasses, strontium borosilicate, barium silicate, lithium silicate, lithium alumina silicate, kaolin, quartz, and talc. Preferably, the silica is in the form of silanized fumed silica. Preferred glass fillers are silanized barium boron aluminosilicate and silanized fluoride barium boron aluminosilicate. Preferably, these surface treated inorganic fillers can be suspended in printable polymerizable resin. Most preferably, they form a homogeneous mixture. Organic particles such as poly(methyl methacrylate) (PMMA), highly crosslinked PMMA beads, poly(methyl/ethyl methacrylate), poly(methyl/butyl methacrylate), rubber modified PMMAs, rubber impact modifiers, crosslinked polyacrylates, thermoplastic and crosslinked polyurethanes, grounded polymerized compounds of this invention, polyethylene, polypropylene, polycarbonates and polyepoxides, and the like also can be used as fillers. These organic fillers can be added into printable polymerizable resin described above. Preferably, these organic fillers can dissolve or suspend in printable polymerizable resin. Most preferably, they form homogeneous colloids or homogeneous solution or suspension. Composite fillers, such as dental composites can be polymerized and grounded or polymerized into particles and used in the formulations of this invention. Nanoparticles, fine glass particles, or other inorganic impregnated/modified PMMA or crosslinked polymer beads/particles from syntheses or grounding, surface treated or not, can also be used. These composite fillers can be selected based on specific printing resin systems for best compatibility and best bonding.

The inorganic filler particles can also be surface-treated with a silane compound, other organic compound or coupling agent to improve bonding between the particles and resin matrix. Suitable silane compounds include, but are not limited to, gamma-methacryloxypropyltrimethoxysilane, gamma-mercaptopropyltriethoxysilane, gamma-aminopropyltrimethoxysilane, and combinations thereof.

Pigments

Printable polymerizable pigmented materials of this invention contain one or more pigments as coloring or shading agents. The pigments include inorganic pigments and organic pigments. The pigments may be modified to increase the dispensability. For example, modified pigments having a silane group, a polymerizable silane group, dialkylaminomethyl group or dialkylaminoethylsulfonic acid group are preferred used. In an additional example, inorganic pigments can be surface-treated with a silane compound, other coupling agent, surfactant or polymer to improve bonding between the particles and resin matrix as well as to enhance the dispersion in printable materials. Suitable silane compounds include, but are not limited to, gamma-methacryloxypropyltrimethoxysilane, gamma-mercaptopropyltriethoxysilane, gamma-aminopropyltrimethoxysilane, and combinations thereof. Many methods, including several mechanical methods, ultrasonic dispersing method, etc. may be used to disperse pigments into resin matrix of this invention.

The term "pigment" refers to visible materials which are not soluble, but are suspended or dispersed as fine particles in the subject materials. Examples of the inorganic pigment include, but not limited to, black iron oxide, yellow iron oxide, ultramarine blue, brown iron oxide, titanium oxide, zinc flower, zinc oxide, iron oxide, aluminum oxide, silicon dioxide, talc, barium sulfate, calcium sulfate, red oxide, cobalt chrome green, Armenian blue, carbon black, mica, cobalt violet, molybdenum red, titanium cobalt green, molybdate orange, etc. Examples of the organic pigments include Cromophtal Red-BRN 2-napthalenecarboxamide, azo pigments, polyazo pigments, azomethine pigments, isoindoline pigments, anthraquinone pigments, phthalocyanine pigments, benzimidazolone pigments, etc. More important, a PMMA or other polymer based pigments systems can be developed by encapsulating various pigments in fine PMMA polymer beads and form core shell structures, where pigment particles are encased in PMMA polymer beads, which are stable in resin matrix, especially MMA based polymerizable liquid. Resin based pigment systems can also be developed by encapsulating various pigments in various fine polymerized resin beads. These polymer beads can be prepared by emulsion or suspension polymerizations. Alternatively, high pigment concentrated resins or MMA based resins can be polymerized and then grounded into fine powders and subsequently used in polymerizable liquids to form colloids or desirable suspensions.

Pigmented materials are desirable because they have superior shade stability and stand up to UV light irradiation. This invention overcame the potential pigment separation from dental resins by dispersing the particles in the solution better to prevent settling and by milling the particles to smaller sizes. Mechanical methods were also applied to finely dispersed pigments in selected matrix, and polymeric additives so as to effectively stabilize and suspense pigments in liquid. This invention further overcame the potential pigment separation from dental resins by using nano-dispersed and fine inorganic and organic pigments. Nano-dispersed organic pigments are preferred to be used here. In addition, a fluorescing agent or several fluorescing agents may be included, such as Lumilux Blue LZ fluorescing agent (dihydroxy terepthalate acid ester).

In addition to the photoactive agents, fillers, pigments, the material of this invention may include a polymerization inhibitor, but are not limited to, such as, for example, butylated hydroxytoluene (BHT); hydroquinone; hydroquinone monomethyl ether; benzoquinone; chloranil; phenol; butyl hydroxyanaline (BHA); tertiary butyl hydroquinone (TBHQ); tocopherol (Vitamin E); and the like. Preferably, butylated hydroxytoluene (BHT) and the methyl ether of hydroquinone (MEHQ) are used as the polymerization inhibitor. The polymerization inhibitors act as scavengers to trap free radicals in the composition and to extend the material's shelf life. Other stabilizers, such UV absorbers, may also be used.

Methods

Many currently available 3D printing methods can be used to build 3D dental devices, such as denture, denture base or splints containing two or more layered materials. These methods, e.g., fused deposition modeling (FDM), Ink-Jet printing using particulate powder layers in powder bed, selective laser sintering (SLS) or fiber reinforced extrusion from FDM can be used to build these dental devices, part of the dental devices, framework of dental devices or one or more layers of dental devices. A few methods will be discussed more in details below.

Ink-Jet Printing Using Supporting System

In an ink-jet printing method, the polymerizable dental material combined with a supporting material is used as a scaffold or foundation for building-up the 3D dental object. An ink-jet printer is used to jet the polymerizable dental material and supporting material onto a working platform. The polymerizable dental material changes from a low viscosity flowable material to shape stable material when it is exposed to light irradiation, phase transition from cooling or other polymerization method. Multiple layered and/or multiple shaded 3D dental object and material supporting the object are built-up thin layer-by-thin layer using this method. Successive thin layers of the polymerizable materials and supporting material are applied to form the layered denture or other dental device. Once 3D dental object has been completely fabricated, the supporting material is removed.

Inkjet print heads, such as piezoelectric ink jet print heads can be used in the printing device to produce a layered 3D dental object, such as a layered denture base, which provide shape memory tissue side layer or adjustable layer for easy adjustment for optimal fit as well as for best adaptation and fit to the changed oral cavity or an adjustable layer around artificial denture teeth, which allows easy occlusal adjustment. Piezo print heads allow the use of pigmented materials and can vary the size of droplets so the printing speed and resolution can be adjusted. It is important that the formulations have sufficiently low viscosity so that they can be handled and discharged easily from the ink-jet printing devices. At the same time, the formulations must be capable of producing dental products having sufficient mechanical strength and integrity.

3D Printing Using DLP System, Stereolithography or Similar Light Irradiation As Well As Their Combinations In general, these two general approaches (DLP-type printer or Stereolithography-type printer) can be used for fabricating the 3D dental devices, such as denture, denture base or splints, etc. using various polymerizable dental resin materials. However, additional methods based on other light irradiation methods as well as the combination of DLP, stereolithography or other light irradiation methods may also be used. It is preferable a 3D printer for fabricating the multiple layered 3D dental devices using multiple DLP light sources at different angles, laser beams or similar light irradiations from different angles or their combinations of different light sources from different angles. More preferable, light beams (or lasers) are able to irradiate 360 degree around the objects with light beams (or lasers) from horizontal to vertical directions. It is also preferable, light beams (or lasers) are able to move 360 degree around the objects with light beams (or lasers) irradiated from 360 degree from horizontal to vertical directions. It is also preferable, light beams (or lasers) are able to sense or/and adjust vertical position or beam direction based on the liquid resin level in vat with light beams (or lasers) irradiated from 360 degree around the objects from horizontal to vertical directions.

The printable polymerizable dental material is flowable or heated to form a flowable liquid prior to polymerization. 3D printer builds successive layers of the polymerizable materials by projecting or irradiating light onto the building plane and cures to form the denture or other dental devices. Multiple layered denture base, denture or other dental devices can be built from multiple polymerizable dental materials in multiple vats. Several printable polymerizable dental materials with different shades and color can be prepared and placed into separate baths (vats). In a case of build a two layered denture base, first layer of denture base is to build from first denture base shaded bath thin layer by thin layer. This first layer of denture base is washed and transferred into a second denture base shaded bath to build second layer of denture base thin layer by thin layer, where light beams were irradiated from different angles (might be movable up to 360 degree and might irradiate from up to 360 degree from horizontal to vertical directions) so as to allow the thin layer by thin layer built up on the surface of first shaded denture base. Multiple light sources (or beams) as well as different light sources (or beams) may be used in a single printing unit. If desired, this two layered denture base can be washed and transferred into another denture base shaded bath to build additional denture base layer on the surface of previous built layers. It may also transfer to another 3D printer to build different layer. In addition, a SLS, FDM or inkjet based powder bed printed first layer may be used in a vat here to build second layer of denture base. Moreover, artificial denture teeth with multiple dentin and enamel layers may be built similarly.

For the fabrication of a denture, denture base can be built in a vat of first denture base shaded liquid using a 3D printing method based on light irradiation thin layer by thin layer. After washed, this first layer of denture base can be inserted into a second vat containing second denture base shaded liquid. After washed, this two layered denture base can be inserted into a third vat containing dentin shaded liquid. Subsequently dentin layer may be built layerwisely (thin layer by thin layer). If additional shaded dentin is desired, this denture can be removed and washed, and then can be inserted into a fourth vat containing different dentin shaded liquid and built another dentin layer. If additional shades are desired, this denture can be washed, and then can be inserted into a fifth vat containing enamel shaded liquid and subsequently enamel layer may be built layerwisely. Additional dentin and enamel shades can be built similarly as described above. Nevertheless, a denture may be built by reversal steps, where teeth or enamel are built first and then denture base.

As described in the following examples, various formulations of the printable polymerizable materials can be prepared for use in a 3D printing device. For DLP or SLA based 3D printer, it is important that the formulations have sufficiently low viscosity so that they can be handled easily and cured device can be removed easily from the liquid resin bath (reservoir or vat). A heated liquid resin bath (reservoir or vat) may be used to achieve desired low viscosity. At the same time, the formulations must be biocompatible, capable of producing dental products having sufficient mechanical strength and integrity. In addition to a heated liquid resin bath (reservoir or vat) may be used to achieve desired low viscosity, some mechanical agitation or stirring may be applied. Several flowable, printable polymerizable materials including composites were prepared with various shades for different applications. The flowable, printable polymerizable materials were successfully, locally cured to form various 3D dental objects. Several selected examples are shown in the Example Section. The materials were cured in this manner thin layer by thin layer and formed 3D dental objects that can be separated from the rest of liquid resin in the bath of 3D printer and subsequently additional layer was built in another liquid resin bath to form two layered dental objects and each layer offered different performance. In addition, the different layers of denture base can be printed out separately and then bonded together and cured to form final denture base. Additionally, wash solvents (e.g., ethyl acetate, alcohols, acetone, THF, heptane, etc. or their combinations) may be used to remove uncured resin from 3D dental objects and finally cured as needed. A heat or light treatment or their combination may be used to enhance their mechanical and physical properties as well as their performance. Air barrier coating, sealer may be used prior to final cure. Inert atmosphere in an enclosed building chamber or inert gas blanket may be used for final cure of dental devices or the mass production of dental devices (e.g., denture teeth, denture bases, crowns and bridges, splints, orthodontic appliances, aligners, etc.) in a manufacturing environment.

EXAMPLES

Example 1

Preparation of Oligomer

A reactor was charged with 1176 grams of trimethyl-1,6-diisocyanatohexane (5.59 mol) and 1064 grams of bisphenol A propoxylate (3.09 mol) under dry nitrogen flow and heated to about 65° C. under positive nitrogen pressure. To this reaction mixture, 10 drops of catalyst dibutyltin dilaurate were added. The temperature of the reaction mixture was maintained between 65° C. and 140° C. for about 70 minutes and followed by additional 10 drops of catalyst dibutyltin dilaurate. A viscous paste-like isocyanate end-capped intermediate product was formed and stirred for 100 minutes. To this intermediate product, 662 grams (5.09 mol) of 2-hydroxyethyl methacrylate and 7.0 grams of BHT as an inhibitor were added over a period of 70 minutes while the reaction temperature was maintained between 68° C. and 90° C. After about five hours stirring under 70° C., the heat was turned off, and oligomer was collected from the reactor as semi-translucent flexible solid and stored in a dry atmosphere.

Example 2

Preparation of Urethane Monomer (UCDPMAA)

A 500 mL flask was charged with 38.8 grams (0.200 mol) of 1,3-bis(isocyanatomethyl)cyclohexane under dry nitrogen flow and heated to about 60° C. under positive nitrogen pressure. To this reaction mixture, 3 drops of catalyst dibutyltin dilaurate were added. A mixture of 22.7 grams of 2-hydroxy-3-phenoxy propyl acrylate, 26.6 grams (0.204 mol) of 2-hydroxyethyl methacrylate, 11.5 grams (0.099 mol) of 2-hydroxyethyl acrylate and 0.10 grams of BHT as an inhibitor were added over a period of 70 minutes while the reaction temperature was maintained between 56° C. and 78° C. After about four hours stirring, the heat was turned off, and monomer was collected from the flask as viscous liquid and stored in a dry atmosphere.

Example 3

Organic Modified Pigment Material

A polymerizable dental material was prepared by stirring at 85° C. a liquid mixture of 30 grams of oligomer made following the procedure of Example 1; 66.5 grams of methyl methacrylate; 3 grams of fine pigment particles; and 0.5 gram of dibenzoyl peroxide (BPO). This material was heat cured and subsequently ground to form fine particulate powder containing particles having an average particle size in the range of about 0.5 to about 100 micrometers. The pigment particulates produced can be used in 3D printer and suspended well without separation. Alternatively, these polymer beads can be made by suspension or emulsion polymerizations.

Example 4

Organic Modified Pigment Material

A polymerizable dental material was prepared by stirring at 85° C. a liquid mixture of 20 grams of 2-phenoxyethyl methacrylate (SR340 from Sartomer); 5.0 grams of triethylene glycol dimethacrylate; 72.5 grams of methyl methacrylate; 2 grams of fine pigment particles; and 0.5 gram of dibenzoyl peroxide (BPO). This material was heat cured and subsequently ground to form fine particulate powder containing particles having an average particle size in the range of about 0.5 to about 100 micrometers. The pigment particulates produced can be used in 3D printer and suspended well without separation. Alternatively, these polymer beads can be made by suspension or emulsion polymerizations.

Printable Polymerizable Compositions

Printable polymerizable compositions are used in a 3D building resin bath of 3D printer to fabricate the dental objects. These compositions may contain acrylate or methacrylate monomers or oligomers, polymers, fillers, catalysts, various modifiers, antimicrobial agents, fluorescing agents, UV absorbing additives, thixotroping agents, plasticizers, antifungal agents, fibers, impact modifiers, pigments, stabilizers and light curable initiators, etc. Preferably, these resins will form flowable liquids at ambient or elevated temperatures and cure rapidly at those temperatures required for different resins to form 3D objects using the methods disclosed in this invention. This results in shape-stable three-dimensional objects being formed immediately.

Example 5

Dental Materials

A polymerizable dental material was prepared by stirring at ambient temperature a liquid mixture of 30 grams of oligomer made following the procedure of Example 1; 30 grams of methyl methacrylate (MMA); 30 grams of 2-phenoxyethyl methacrylate (SR340 from Sartomer); 8 grams of rubber impact modifier M570 (from Kaneka); 1.9 grams of 2,4,6-trimethylbenzoyldiphenylphosphine oxide, (Lucirin TPO available from BASF); and 0.1 gram of butylated hydroxytoluene (BHT). This material can be used in DLP or SLA type 3D printer to make a layer of dental device, such as a rigid layer of a denture base or adjustable denture base layer for artificial denture teeth in a denture.

Example 6

Dental Materials

A polymerizable dental material was prepared by stirring at ambient temperature a liquid mixture of 40.5 grams of oligomer made following the procedure of Example 1; 33 grams of 2-phenoxyethyl methacrylate (SR340 from Sartomer); 20 grams of ethoxylatedio bisphenol A dimethacrylate (SR480 from Sartomer); 6 grams of rubber impact modifier B637 (from Kaneka); 0.5 grams of 2,4,6-trimethylbenzoyldiphenylphosphine oxide, (Lucirin TPO available from BASF). This material can be used in DLP or SLA type 3D printer to make a layer of dental device, such as a hard layer in a nightguard or orthodontic aligner/retainer or adjustable denture base layer for artificial denture teeth in a denture.

Example 7

Dental Materials

A polymerizable dental material was prepared by stirring at ambient temperature a liquid mixture of 30 grams of oligomer made following the procedure of Example 1; 39 grams of methyl methacrylate (MMA); 30 grams of 2-phenoxyethyl methacrylate (SR340 from Sartomer); 1 grams of 2,4,6-trimethylbenzoyldiphenylphosphine oxide, (Lucirin TPO available from BASF). This material can be used in inkjet type 3D printer to make a layer of dental device, such as a rigid layer or adjustable denture base layer for artificial denture teeth in a denture.

Example 8

Dental Materials

A polymerizable dental material was prepared by stirring at ambient temperature a liquid mixture of 34 grams of oligomer made following the procedure of Example 1; 16 grams of 2-phenoxyethyl methacrylate (SR340 from Sartomer); 14 grams of 3,3,5-trimethylcyclohexyl methacrylate (CD421A from Sartomer); 28 grams of ethoxylated$_{10}$ bisphenol A dimethacrylate (SR480 from Sartomer); 6 grams of rubber impact modifier M731 (from Kaneka); 1.9 grams of 2,4,6- trimethylbenzoyldiphenylphosphine oxide, (Lucirin TPO available from BASF); and 0.1 gram of butylated hydroxytoluene (BHT). This material can be used in DLP or SLA type 3D printer to make a layer of dental device, such as a hard layer in a nightguard or orthodontic aligner/retainer.

Example 9

Dental Materials

A polymerizable dental material was prepared by stirring at ambient temperature a liquid mixture of 10 grams of oligomer made following the procedure of Example 1; 30 grams of lauryl methacrylate; 50 grams of 2-phenoxyethyl methacrylate (SR340 from Sartomer); 9 grams of rubber impact modifier M570 (from Kaneka); 1 grams of 2,4,6-trimethylbenzoyldiphenylphosphine oxide, (Lucirin TPO available from BASF). This material can be used in DLP or SLA type 3D printer to make a layer of dental device, such as an adjustable, shape memory layer of a denture base.

Example 10

Dental Materials

A polymerizable dental material was prepared by stirring at ambient temperature a liquid mixture of 23.5 grams of lauryl methacrylate; 30 grams of 2-phenoxyethyl methacrylate (SR340 from Sartomer); 30 grams of tetrahydrofurfuryl methacrylate (SR203 from Sartomer); 10 grams of urethane acrylate (CN980 from Sartomer); 5 grams of rubber impact modifier M731 (from Kaneka); 1 grams of 2,4,6- trimethylbenzoyldiphenylphosphine oxide, (Lucirin TPO available from BASF) and 0.5 grams of 2,4,6- trimethylbenzoyldiphenylphosphine oxide, (Lucirin TPO available from BASF); and 0.5 gram of visible light initiating solution containing 13.3% camphorquinone (CQ), 23.0% methacrylic acid (MAA), 1.3% butylated hydroxytoluene (BHT), 46% N, N-dimethylaminoethylneopentyl acrylate, and 16.3% γ- methacryloxypropyltrimethoxysilane. This material can be used in inkjet type 3D printer to make a layer of dental device, such as an adjustable, shape memory layer of a denture base.

Example 11

Dental Materials

A polymerizable dental material was prepared by stirring at ambient temperature a liquid mixture of 25 grams of monomer made following the procedure of Example 2; 10 grams of triethylene glycol dimethacrylate; 14 grams of ethoxylated$_2$ bisphenol A dimethacrylate (SR348 from Sartomer); 1 gram of silanated fumed silica ($SiO_2$) having an average particles size of from about 0.01 to about 0.04 micrometers; 49 grams of silanated barium aluminofluorosilicate glass particles BAFG having an average particle size of from about 0.1 to about 10 micrometer; 0.95 grams of 2,4,6-trimethylbenzoyldiphenylphosphine oxide, (Lucirin TPO available from BASF); and 0.05 gram of butylated hydroxytoluene (BHT). This material can be used in DLP or SLA type 3D printer to make a layer or several layers of a dental device, such as multiple layered and multiple shaded artificial denture teeth of a denture.

Example 12

Dental Materials

A polymerizable dental material was prepared by stirring at ambient temperature a liquid mixture of 20 grams of monomer made following the procedure of Example 2; 20 grams of triethylene glycol dimethacrylate; 5 grams of ethoxylated2 bisphenol A dimethacrylate (SR348 from Sartomer); 4 grams of tris(2-hydroxy ethyl) isocyanurate triacrylate (SR368 from Sartomer); 50 grams of silanated barium aluminoflurosilicate glass particles BAFG having an average particle size of from about 0.1 to about 10 micrometer; 0.975 grams of 2,4,6-trimethylbenzoyldiphenylphosphine oxide, (Lucirin TPO available from BASF); and 0.025 gram of butylated hydroxytoluene (BHT). This material can be used in DLP or SLA type 3D printer to make a layer or several layers of a dental device, such as multiple layered and multiple shaded artificial denture teeth of a denture.

Example 13

Dental Materials

A polymerizable dental material was prepared by stirring at ambient temperature a liquid mixture of 25 grams of monomer made following the procedure of Example 2; 20 grams of triethylene glycol dimethacrylate; 4 grams of tris(2-hydroxy ethyl) isocyanurate triacrylate (SR368 from Sartomer); 48 grams of silanated barium aluminoflurosilicate glass particles BAFG having an average particle size of from about 0.1 to about 10 micrometer; 2 grams of organic modified pigment materials made following the procedure of Examples 3 and 4; 0.975 grams of 2,4,6- trimethylbenzoyldiphenylphosphine oxide, (Lucirin TPO available from BASF); and 0.025 gram of butylated hydroxytoluene (BHT). This material can be used in DLP or SLA type 3D printer to make a layer or several layers of a dental device, such as multiple layered and multiple shaded artificial denture teeth of a denture.

Example 14

Fabrication of a Denture Base

A transparent container (vat) loaded with liquid resin of Example 9 was loaded into vat of 3D printer (B9Creator) and sequential voxel planes are projected into this first liquid resin in a layer-wise manner as controlled by a computer to form a tissue side layer of denture base. Another transparent container (vat) loaded with liquid resin of Example 5 was loaded into vat of 3D printer (B9Creator) and sequential voxel planes are projected into this second liquid resin in a layer-wise manner as controlled by a computer to form tooth side layer of denture base. After both layers were washed with isopropyl alcohol, a thin layer of liquid resin of Example 5 was applied on bonding interface and two layers was combined and fitted together. After the application of air inhibiting barrier, it was cured in Eclipse light unit (sold by Dentsply International) for 6 minutes to form final denture base. Optional, artificial denture teeth may be fitted and bonded into tooth cavities in printed denture base and final cured together to form final denture.

Example 15

Fabrication of a Denture

A transparent container (vat) loaded with liquid resin of Example 9 was loaded into vat of 3D printer (B9Creator) and sequential voxel planes are projected into this first liquid resin in a layer-wise manner as controlled by a computer to form a tissue side layer of denture base. Another transparent container (vat) loaded with liquid resin of Example 8 was loaded into vat of 3D printer (B9Creator) and sequential voxel planes are projected into this second liquid resin in a layer-wise manner as controlled by a computer to form tooth side layer of denture base. The combination of these two layers formed a denture base. Yet another transparent container (vat) loaded with liquid resin of Example 13 was loaded into vat of 3D printer (B9Creator) and sequential voxel planes are projected into this second liquid resin in a layer-wise manner as controlled by a computer to form denture teeth for above formed denture base. After both denture base layers and denture teeth were washed with isopropyl alcohol, a thin layer of liquid resin of Example 8 was applied on bonding interface between two layers of denture base and between denture base and denture teeth and they were combined and fitted together. After the application of air inhibiting barrier, it was cured in Eclipse light unit (sold by Dentsply International) for 10 minutes to form final denture.

Flexural Property Tests

For dental materials, flexural Strength and Flexural Modulus of the polymerized acrylic compositions were measured by using three-point bend test on Instron bending unit according to ISO20795-1:2013. Samples were cured for 10+10 minutes in Eclipse EPU light unit (sold by Dentsply International). The flexural specimens (3.3 mm×10 mm×64 mm) were stored in 37° C. water for 50 hours, immediately laid on the supports of the flexural test rig immersed in the 37° C. water bath and allowed the specimen to come to equilibrium with the water bath temperature. Then the flexural properties were determined using three point flexure test with a span of 50 mm at an Instron crosshead speed of 5 mm/minute and loaded to break according to ISO20795-1:2013. Flexural Strength and Flexural Modulus of the polymerized compositions of denture tooth composite materials were measured with crosshead speed of 1 mm/minute by using three-point bend test on Instron bending unit according to ISO. Samples (2 mm×2 mm×25 mm) from Examples 11 to 13 were cured for 5+5 minutes in Enterra light unit (sold by Dentsply International). The flexural strength and flexural modulus of tooth composite materials and polymerized acrylic compositions are shown in Table 1.

TABLE 1

Flexural strength and flexural modulus of dental materials of this invention tested.

| Material | Flexural Strength (MPa) | Modulus (MPa) |
| --- | --- | --- |
| Example 5 | 60-100 (70-90) | 2300-2700 (2400-2600) |
| | 80.3 (sd = 0.7) | 2510 (sd = 40) |
| Example 6 | 30-70 (40-55) | 1400-1800 (1500-1700) |
| | 48.0 (sd = 1.0) | 1590 (sd = 60) |
| Example 8 | 30-70 (40-60) | 1300-1700 (1400-1600) |
| | 49.3 (sd = 2.5) | 1490 (sd = 60) |
| Example 13 | 120-165 (130-155) | 4000-8000 (5000-7000) |
| | 143.3 (sd = 12.1) | 5770 (sd = 190) |

*

Fracture Toughness Tests

Fracture toughness specimens for denture base materials were prepared, notched to a depth of 3 mm and stored in 37° C. water for 7 days and tested with a span of 32 mm at a crosshead speed of 1 mm/minute until maximum load was passed and the crack had almost reached the opposite side of the specimen according to ISO20795-1:2013. Samples were cured for 10+10 minutes in Eclipse EPU light unit (sold by Dentsply International). The toughness data are listed in Table 2.

TABLE 2

Fracture toughness of dental materials of this invention tested at ambient temperature.

| Material | $K_{max}$ (MPa m$^{1/2}$) | Work (J/m$^2$) |
| --- | --- | --- |
| Example 5 | 2.1-2.8 (2.25-2.6) | 800-1050 (875-1000) |
| | 2.43 (sd = 0.15) | 930 (sd = 70) |
| Example 8 | 2.3-2.75 (2.45-2.65) | 2800-3100 (2850-3050) |
| | 2.55 (sd = 0.08) | 2920 (sd = 80) |
| Example 13 | 1.7-2.3 (1.8-2.2) | 175-300 (200-275) |
| | 2.04 (sd = 0.15) | 240 (sd = 40) |

It should be understand that while the present invention has been described with respect to certain specific embodiments thereof, it should not be considered limited to such embodiments but may be used in other ways without departure from the spirit of the invention and the scope of the appended claims. The present invention describes mainly denture and denture base; it should be understand that can be referred to splint, nightguard, retainer, aligner, flipper, flexible partial, and many other dental devices.

The invention claimed is:

1. A dental component formed from rapid prototyping comprising at least one first layer having a first composition and at least one second layer having a second composition that is different form the first composition,
    wherein the first composition includes:
        an oligomer formed from the reaction of an isocyanate end-capped intermediate product and a hydroxyl based methacrylate;
        at least one polymerizable acrylic compound selected from the group consisting of a phenoxy based methacrylate, a cyclohexyl based methacrylate, a dimethacrylate, and mixtures thereof;
        a rubber impact modifier; and
        a photoinitiator;
    wherein the second composition includes:
        a urethane monomer;
        a glycol dimethacrylate;
        a filler including glass particles having an average particle size from about 0.1 to about 10 micrometers; and
        a photoinitiator.

2. The dental component of claim 1, wherein the first composition, when cured, has flexural strength ranging from 30 to 70 MPa.

3. The dental component of claim 1, wherein the first composition, when cured, has fracture toughness ranging from 2.4 to 2.6 MPa m$^{1/2}$.

4. The dental component of claim 1, wherein the second composition, when cured, has flexural strength ranging from 120 MPa to 200 MPa.

5. The dental component of claim 1, wherein the first composition, when cured, has fracture toughness ranging from 1.8 MPa to 2.2 MPa m$^{1/2}$.

6. The dental component of claim 1, wherein the first composition, the second composition or both further includes a stabilizer.

7. The dental component of claim 6, wherein the stabilizer is selected from the group consisting of butylated hydroxytoluene and methyl ether of hydroquinone.

8. The dental component of claim 1, wherein at least one polymerizable acrylic compound includes the phenoxy based methacrylate that is selected from the group consisting of 2-hydroxy-3-phenoxypropyl acrylate, 2-phenoxyethyl (meth)acrylate, and phenoxy benzyl (meth)acrylate.

9. The dental component of claim 1, wherein at least one polymerizable acrylic compound includes the cyclohexyl based methacrylate that is selected from the group consisting of cyclohexyl (meth)acrylate, 4-tert-butylcyclohexyl (meth)acrylate, isobornyl cyclohexyl (meth)acrylate; cyclohexyl (meth)acrylate, and trimethylcyclohexyl (meth)acrylate.

10. The dental component of claim 1, wherein at least one polymerizable acrylic compound includes the dimethacrylate that is selected from the group consisting of ethoxylated bisphenol A-dimethacrylate, urethane di(meth)acrylate (UDMA), diurethane dimethacrylate (DUDMA), 4,13-dioxo-3,14 dioxa-5,12-diazahexadecane-1,16-diol dimethacrylate, and 4,19-dioxo-3,20 dioxa-5,18-diazahexadecane-1,22-diol dimethacrylate.

11. The dental component of claim 1, wherein the filler is selected from the group consisting of silanized barium boron aluminosilicate and silanized fluoride barium boron aluminosilicate.

* * * * *